US006900289B2

(12) United States Patent
Yanagihara

(10) Patent No.: US 6,900,289 B2
(45) Date of Patent: May 31, 2005

(54) *PHYSALIA* FLUORESCENT PROTEINS

(75) Inventor: Angel Anne Yanagihara, Honolulu, HI (US)

(73) Assignee: The University of Hawaii, Honolulu, HI (US)

( * ) Notice: Subject to any disclaimer, the term of this patent is extended or adjusted under 35 U.S.C. 154(b) by 0 days.

(21) Appl. No.: 10/226,877

(22) Filed: Aug. 22, 2002

(65) Prior Publication Data

US 2003/0143521 A1 Jul. 31, 2003

Related U.S. Application Data

(60) Provisional application No. 60/314,378, filed on Aug. 22, 2001.

(51) Int. Cl.$^7$ .......................... C07K 1/00; C07K 14/00; C07K 17/00

(52) U.S. Cl. .......................... 530/350; 435/4; 435/69.1; 435/320.1; 435/325

(58) Field of Search .................................. 530/350, 300, 530/387.1, 325; 435/4, 69.1, 320.1, 325, 7.4; 424/405; 544/102; 536/23.4, 23.2; 382/128

(56) References Cited

U.S. PATENT DOCUMENTS

| | | |
|---|---|---|
| 4,471,470 A | 9/1984 | Swainson et al. |
| 5,325,324 A | 6/1994 | Rentzepis et al. |
| 5,625,048 A | 4/1997 | Tsien et al. |
| 6,046,925 A | 4/2000 | Tsien et al. |
| 6,124,128 A | 9/2000 | Tsien et al. |

FOREIGN PATENT DOCUMENTS

| WO | WO 96/23810 | 8/1996 |
|---|---|---|

OTHER PUBLICATIONS

Irie, M. and Mori, M., "Thermally Irreversible Photochromic Systems. Reversible Photocyclization of Diarylethene Derivatives." J. Org. Chem. 53:803–808 (1987).
Parthenopolous, D.A., and Rentzepis, P.M., "Three–Dimensional Optical Storage Memory." Science. 245:843–845(1989).
Hanazawa, M., et al., "Thermally Irreversible Photochromic Systems. Reversible Photocyclization of 1,2–Bis–(2–methylbenzo[*b*]thiophen–3–yl)perfluorocycloalkene Derivatives." J. Chem. Soc. Chem. Commun. 3:206–207(1992).
Dvornikov, A.S., et al., "Spectroscopy and Kinetics of Photochromic Materials for 3D Optical Memory Devices," J. Phys. Chem. 98:6746–6752 (1994).
Dvornikov, A.S., and Rentzepis, P.M., "Process and Materials for Two–Photon Volume Optical Memories." Opt. Mem. Neur. Netw. 3:75–86 (1994).

Ehrig, T., et al., "Green–fluorescent protein mutants with altered fluorescence excitation spectra." FEBS Lett. 367:163–166 (1995).
Delagrave, S., et al., "Red–Shifted Excitation Mutants of the Green Fluorescent Protein." Bio/Technology. 13:151–154 (1995).
Chattoraj, M., et al., "Ultra–fast excited state dynamics in green fluorescent protein: Multiple states and proton transfer ." Proc. Nat. Acad. Sci. USA 93: 8362–8367 (1996).
Brejc, K., et al., "Structural basis for dual excitation and photoisomerization of the *Aequorea victoria* green fluorescent protein." Proc. Nat. Acad. Sci. USA 94:2306–2311 (1997).
Ormo, M., et al., "Crystal Structure of the *Aequorea victoria* Green Fluorescent Protein." Science. 273:1392–1395 (1996).
Yang, F., et al, "The molecular structure of green fluorescent protein." Nature Biotech. 14:1246–1251 (1996).
Ward, W.W., et al., "Spectral Perturbations of the *Aequorea* Green–Fluorescent Protein." Photochem. Photobiol. 35:803–808 (1982).
Levine, L.D., et al, "Isolation and Characterization of a Photoprotein, 'Phialidin', and a Spectrally Unique Green–Fluorescent Protein From The Bioluminescent Jellyfish *Phialidium gregarium.*" Comp. Biochem. Physiol. 72B:77–85 (1982).
Prasher, D.C., et al., Primary structure of the *Aequorea victoria* green–fluorescent protein. Gene. 111:229–233 (1992).
Tsien, R.Y., et al., "FRET for studying intracellular signalling." Trends Cell Biol. 3:242–245 (1993).
Heim, R., and Tsien, R.Y., "Engineering green fluorescent protein for improved brightness, longer wavelengths and fluorescence resonance energy transfer." Current Biol. 6:178–182 (1996).
Cubitt, A.B., et al., "Understanding, improving and using green fluorescent proteins." Trends in Biochem. Sci. 20:448–455 (1995).
Heim, et al., "Wavelength mutations and posttranslational autoxidation of green fluorescent protein." Proc. Nat. Acad. Sci. USA. 91:12501–12504 (1994).

(Continued)

*Primary Examiner*—Robert A. Wax
*Assistant Examiner*—Robert B. Mondesi
(74) *Attorney, Agent, or Firm*—Dorsey & Whitney LLP; Todd A. Lorenz; Traci H. Ropp

(57) ABSTRACT

Provided are *Physalia* fluorescent proteins (PFPs) and, more particularly, to PFPs of a *Physalia* species, and methods of detecting and isolating PFPs. Also provided are methods and compositions for using PFPs, including recombinant PFPs, as reporter molecules in in vitro and in vivo biological assays, including screening assays and cellular assays.

14 Claims, 8 Drawing Sheets

OTHER PUBLICATIONS

Alam, J. M. et al., "Isolation and physiopharmacological properties of three high molecular weight lethal proteins from a coelenterate (*Physalia utriculus*) venom," Pakistan Journal of Zoology 28(3):245–252 (1996) (Abstract) Database: Biosis Biological Abstracts, Philadelphia; Acc. No. 1997:66562 Biosis, Doc. No. PREV199799365765.

Alam, J.M. et al., Biochemical characterization and pathophysiological properties of two high molecular weight cytolytic proteins from the venom of a coelenterate (Jellyfish), *Physalia utriculus* (Blue Bottle). Pakistan Journal of Zoology, 34(1):9–17 (2002) (Abstract) Database: Biosis Biological Abstracts, Philadelphia; Acc. No. 2002:500997, Doc. No. PREV200200500997.

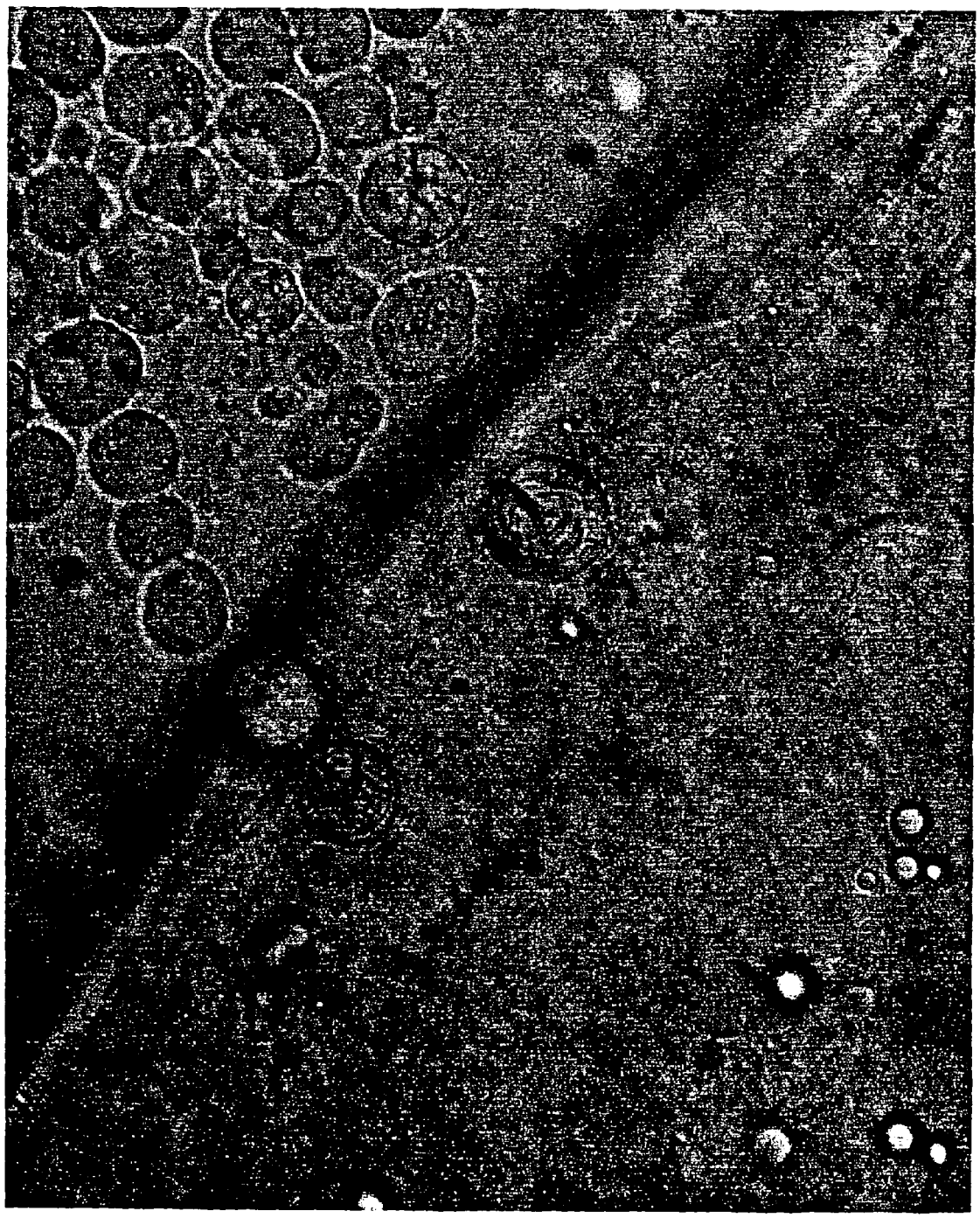
FIG._1

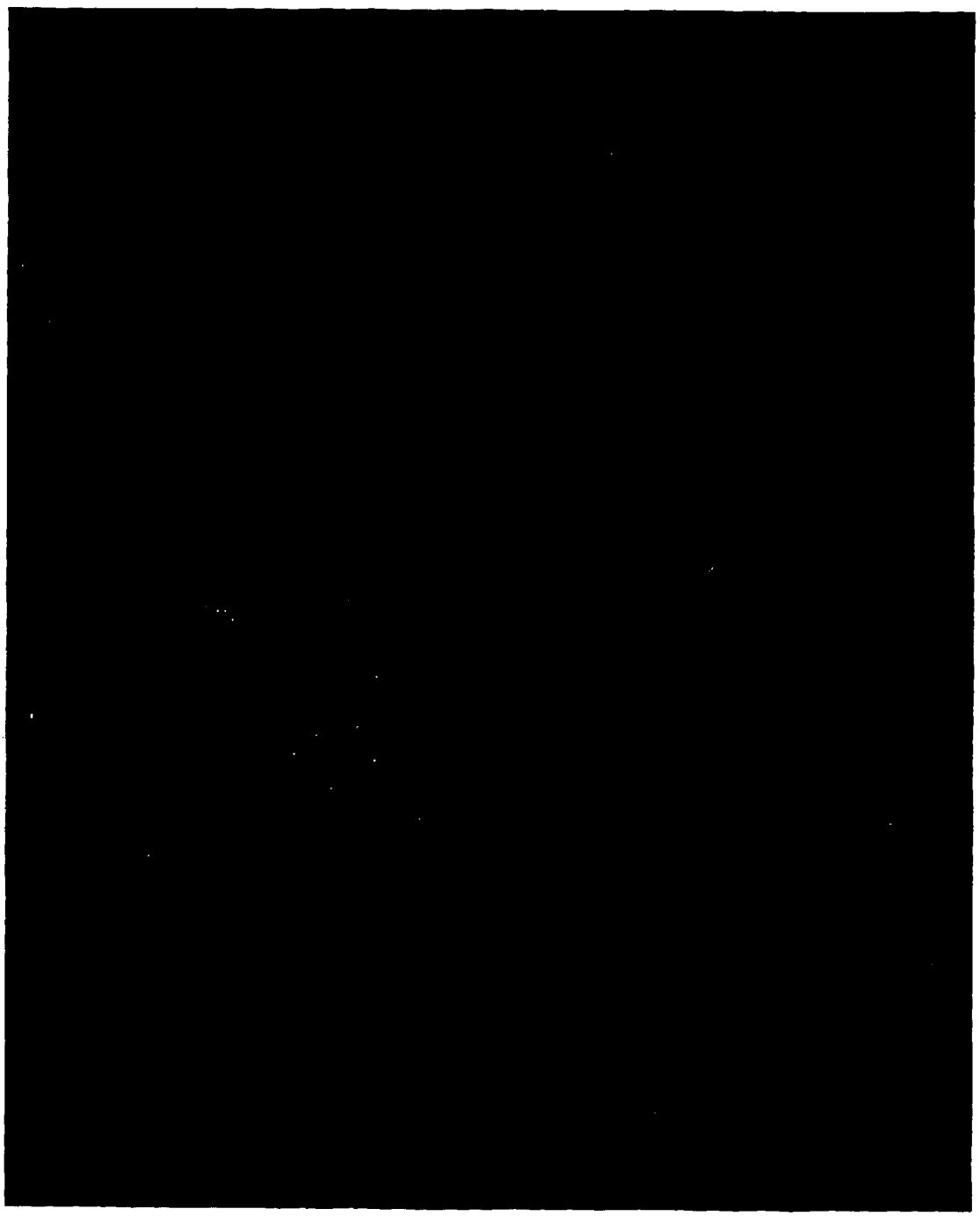
FIG._2

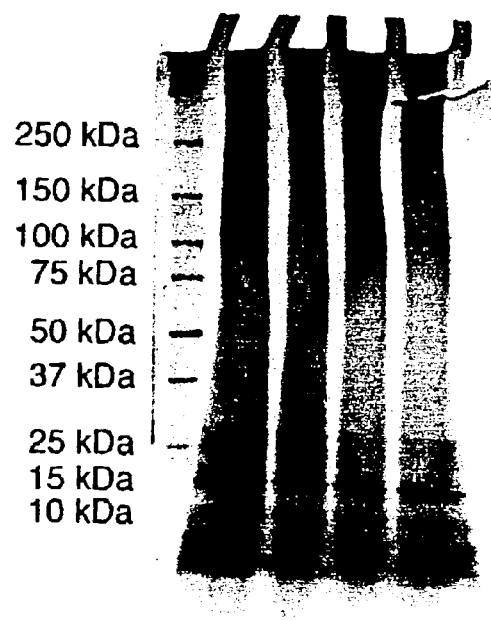
FIG._3A
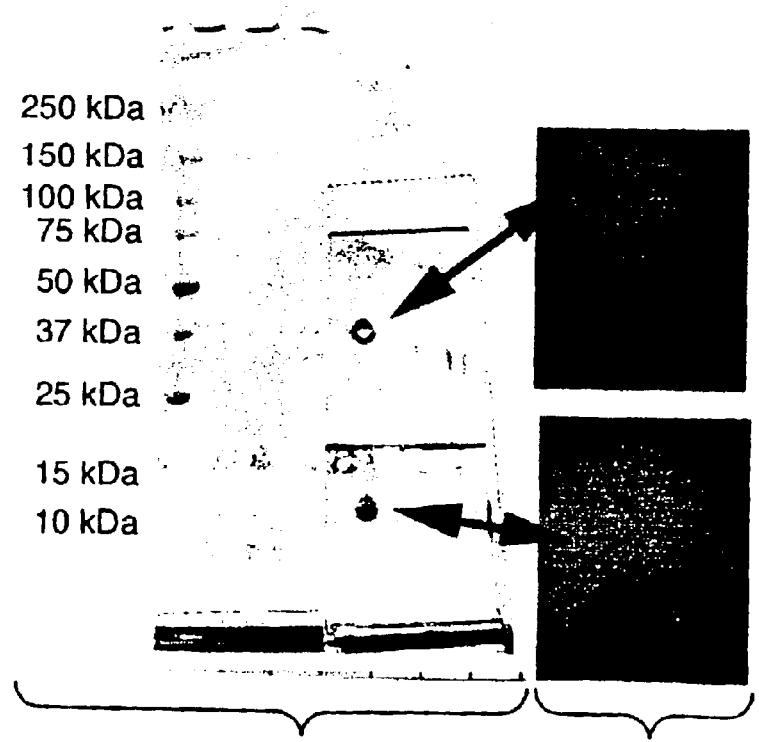
FIG._3B  FIG._3C

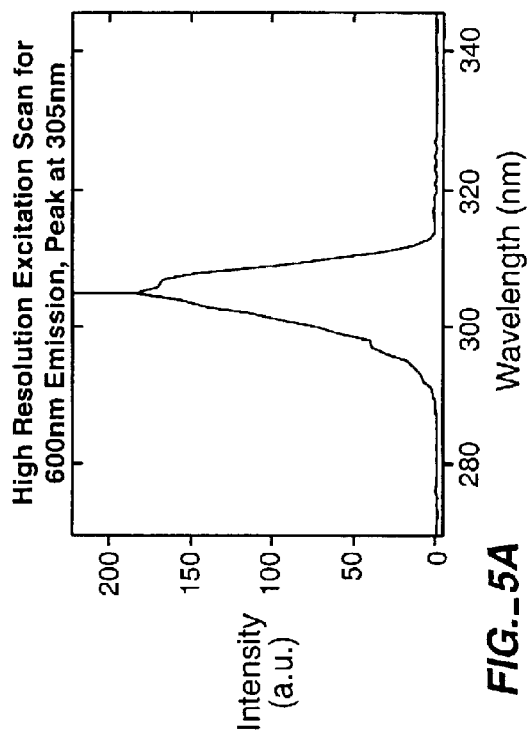
FIG._4A
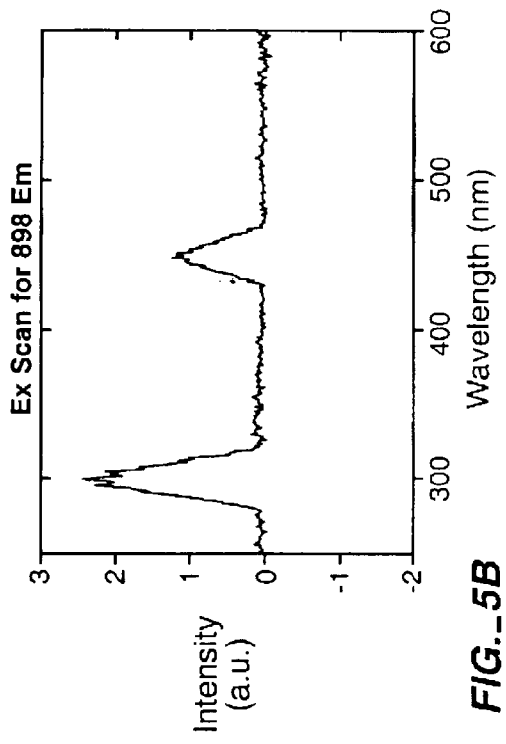
FIG._5A
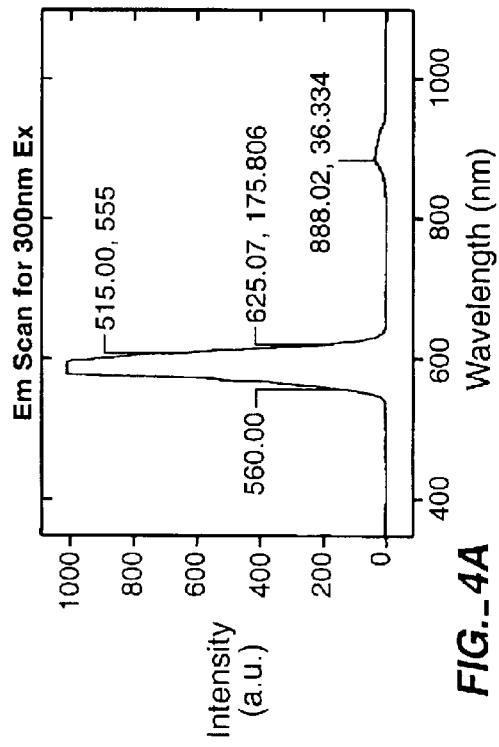
FIG._4B
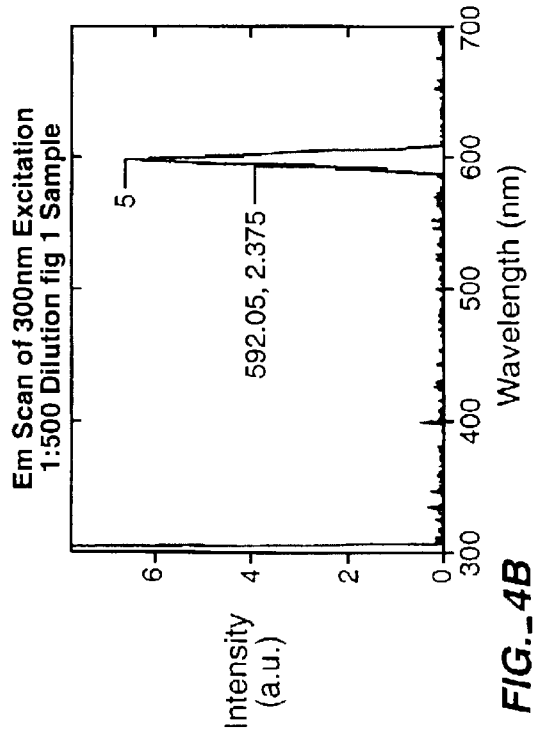
FIG._5B

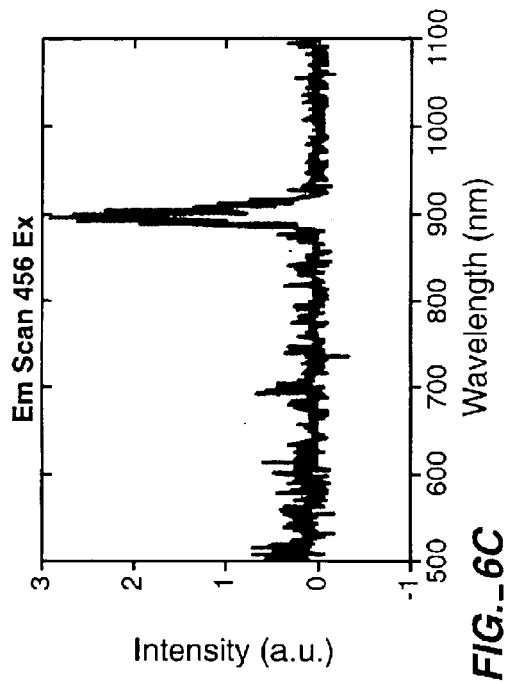
FIG._6A
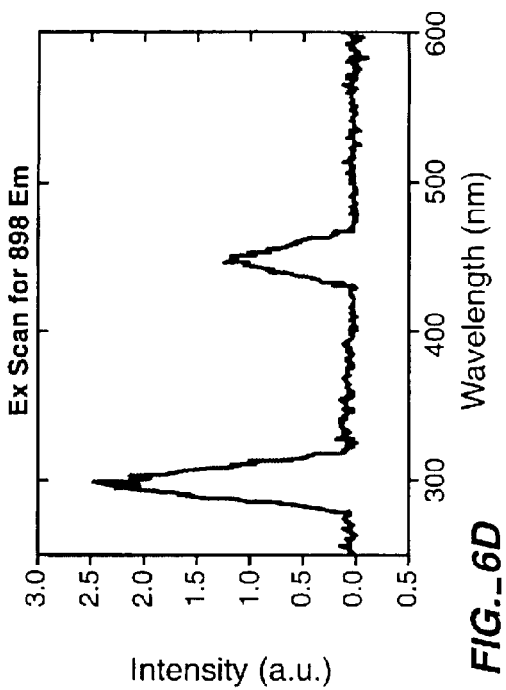
FIG._6B
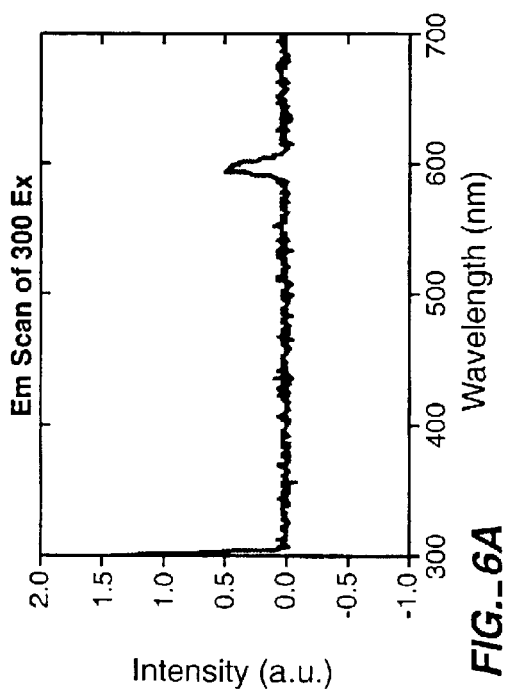
FIG._6C
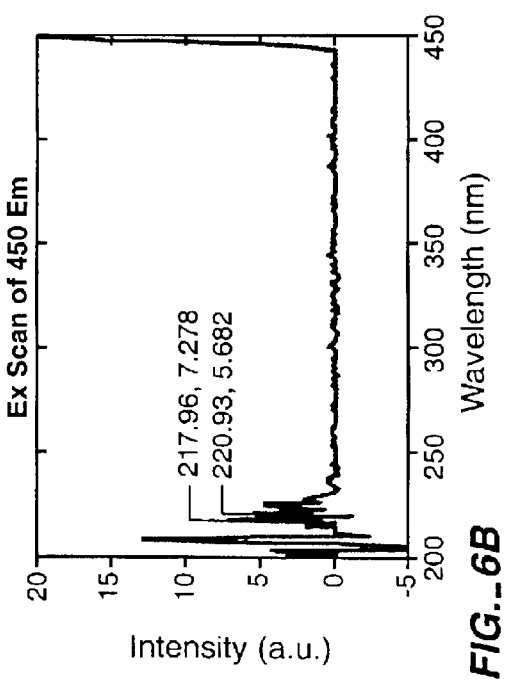
FIG._6D

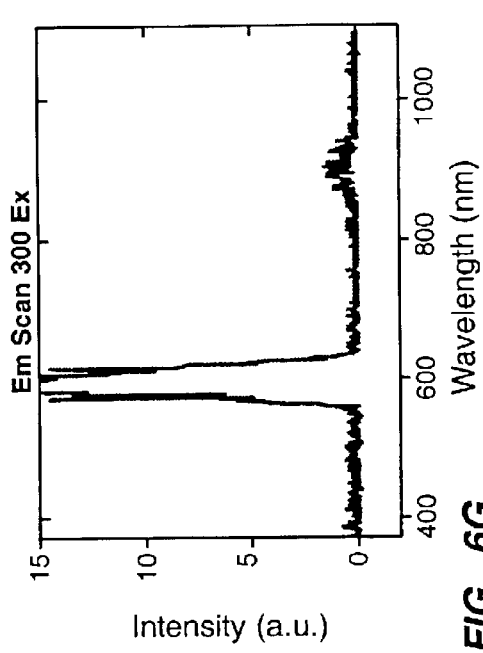
FIG._6G
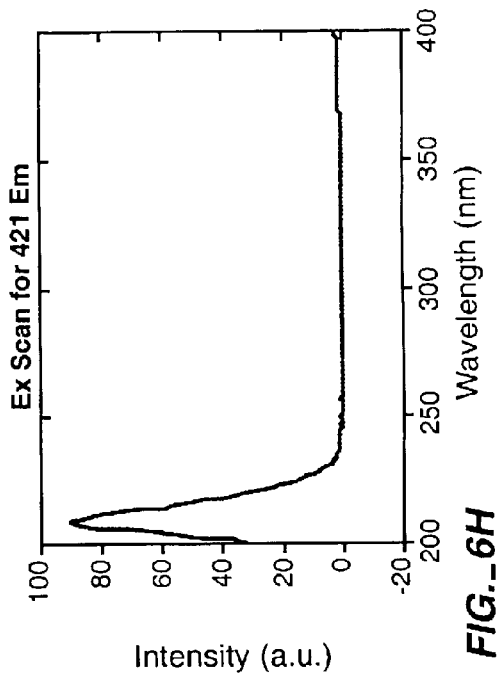
FIG._6H
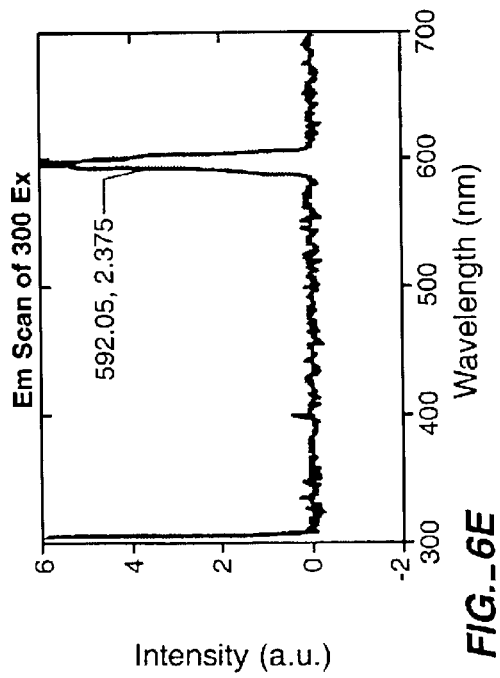
FIG._6E
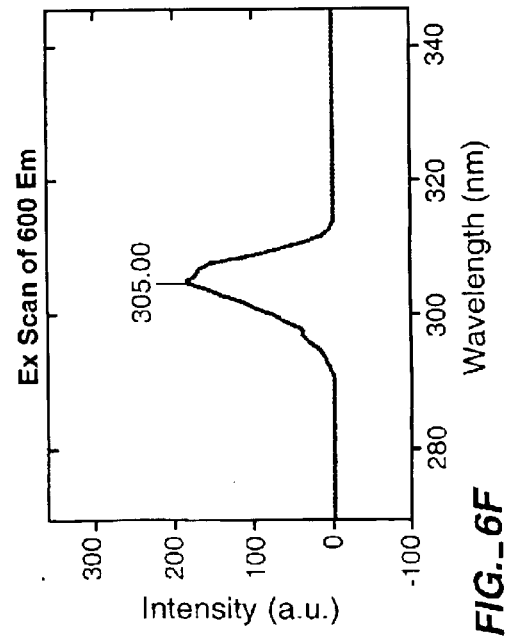
FIG._6F

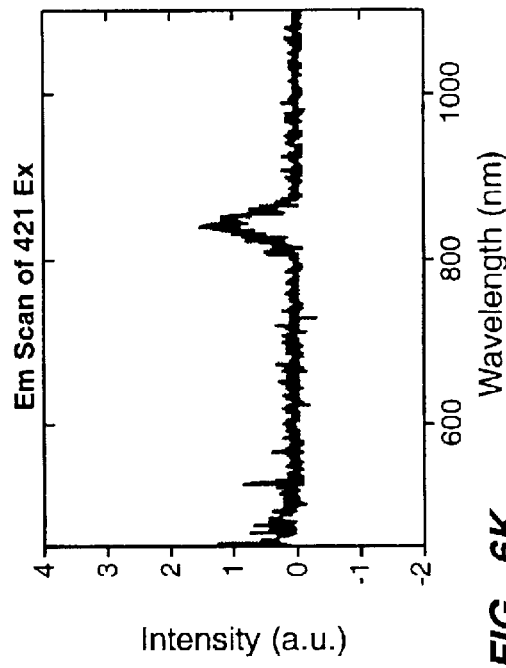
FIG._6K
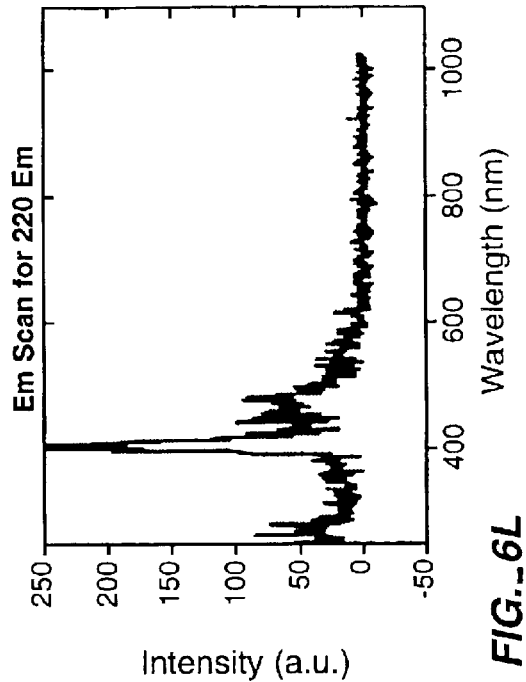
FIG._6L
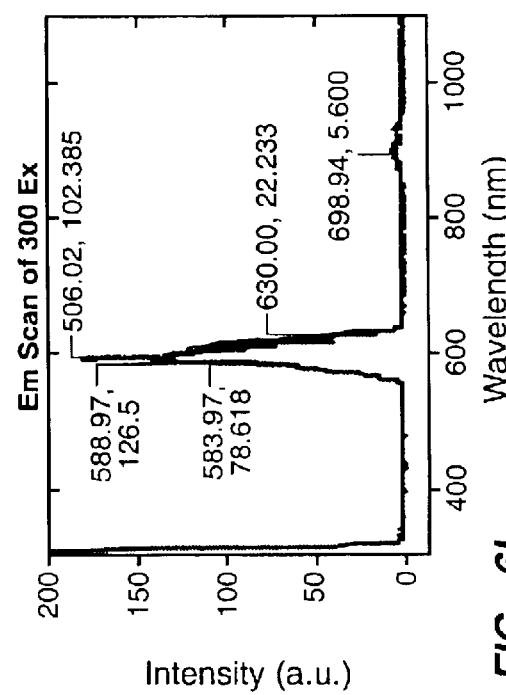
FIG._6I
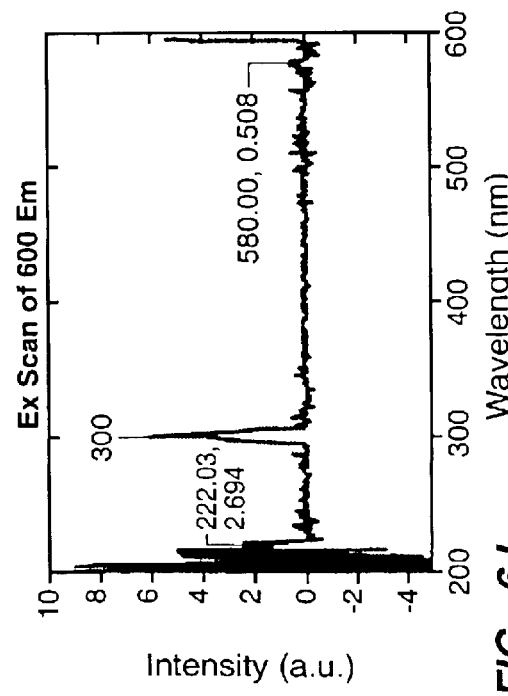
FIG._6J

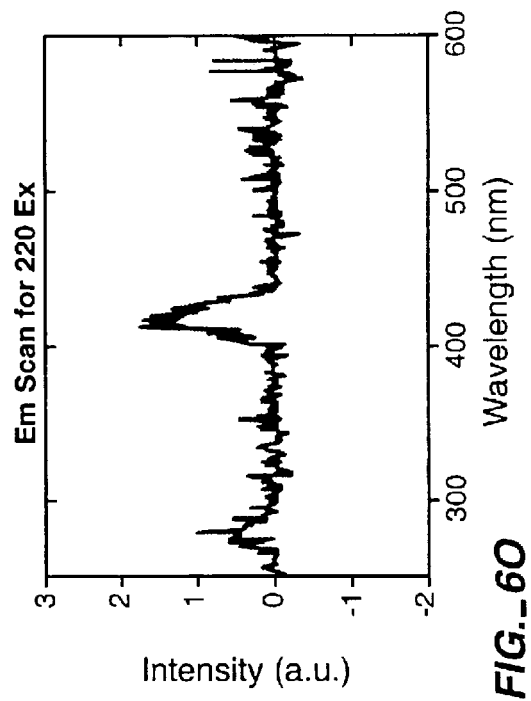
FIG._6O
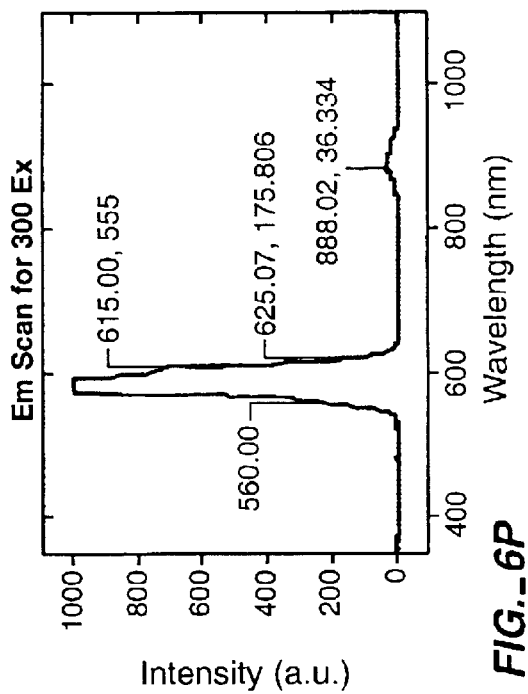
FIG._6P
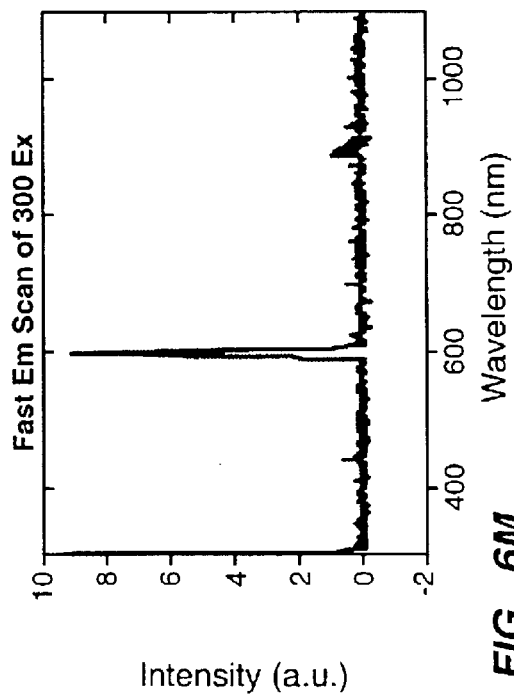
FIG._6M
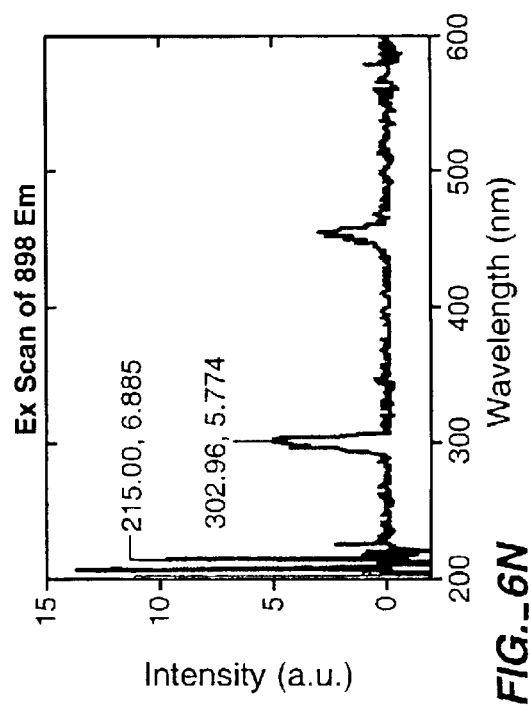
FIG._6N

SEQUENCE LISTING

<160> NUMBER OF SEQ ID NOS: 58

<210> SEQ ID NO 1
<211> LENGTH: 61
<212> TYPE: PRT
<213> ORGANISM: Artificial sequence
<220> FEATURE:
<223> OTHER INFORMATION: coiled-coil presentation structure

<400> SEQUENCE: 1

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 2
<211> LENGTH: 69
<212> TYPE: PRT
<213> ORGANISM: Artificial sequence
<220> FEATURE:
<223> OTHER INFORMATION: minibody presentation structure

<400> SEQUENCE: 2

Met Gly Arg Asn Ser Gln Ala Thr Ser Gly Phe Thr Phe Ser His Phe
1               5                   10                  15

Tyr Met Glu Trp Val Arg Gly Gly Glu Tyr Ile Ala Ala Ser Arg His
            20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Leu Gln Lys
    50                  55                  60

Lys Lys Gly Pro Pro
65

<210> SEQ ID NO 3
<211> LENGTH: 32
<212> TYPE: PRT
<213> ORGANISM: Artificial sequence
<220> FEATURE:
<223> OTHER INFORMATION: zinc finger consensus sequence
<220> FEATURE:
<221> NAME/KEY: MISC_FEATURE
<222> LOCATION: (1)..(5)
<223> OTHER INFORMATION: "Xaa" at positions 1-5 can be any amino acid
<220> FEATURE:
<221> NAME/KEY: MISC_FEATURE
<222> LOCATION: (7)..(9)
<223> OTHER INFORMATION: "Xaa" at positions 7-9 can be any 2 to 3 amino
    acids
<220> FEATURE:
<221> NAME/KEY: MISC_FEATURE
<222> LOCATION: (11)..(22)
<223> OTHER INFORMATION: "Xaa" at positions 11-22 can be any 4 to 12
    amino acids
<220> FEATURE:
<221> NAME/KEY: MISC_FEATURE
<222> LOCATION: (24)..(32)
<223> OTHER INFORMATION: "Xaa" at positions 24-26 and 28-32 can be any
    amino acid

<400> SEQUENCE: 3

```
Xaa Xaa Xaa Xaa Xaa Cys Xaa Xaa Xaa Cys Xaa Xaa Xaa Xaa Xaa
1               5                   10                  15

Xaa Xaa Xaa Xaa Xaa Xaa His Xaa Xaa Xaa His Xaa Xaa Xaa Xaa
                20              25              30

<210> SEQ ID NO 4
<211> LENGTH: 33
<212> TYPE: PRT
<213> ORGANISM: Artificial sequence
<220> FEATURE:
<223> OTHER INFORMATION: C2H2 zinc finger consensus sequence
<220> FEATURE:
<221> NAME/KEY: MISC_FEATURE
<222> LOCATION: (7)..(26)
<223> OTHER INFORMATION: "Xaa" at positions 7 to 26 represents a random
      peptide of 3 to 20 amino acids

<400> SEQUENCE: 4

Phe Gln Cys Glu Glu Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa His Ile Arg Ser His Thr
                20              25              30

Gly

<210> SEQ ID NO 5
<211> LENGTH: 30
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (2)..(3)
<223> OTHER INFORMATION: "Xaa" at positions 2-3 can be any amino acid
<220> FEATURE:
<221> NAME/KEY: MISC_FEATURE
<222> LOCATION: (5)..(24)
<223> OTHER INFORMATION: "Xaa" at positions 5-24 can be any 4 to 20
      amino acids
<220> FEATURE:
<221> NAME/KEY: MISC_FEATURE
<222> LOCATION: (26)..(29)
<223> OTHER INFORMATION: "Xaa" at positions 26-29 can be any amino acid

<400> SEQUENCE: 5

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa His Xaa Xaa Xaa Xaa Cys
                20              25              30

<210> SEQ ID NO 6
<211> LENGTH: 33
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (7)..(26)
<223> OTHER INFORMATION: "Xaa" at positions 7-26 can be any 4 to 20
      random amino acids

<400> SEQUENCE: 6

Val Lys Cys Phe Asn Cys Xaa Xaa Xaa Xaa Xaa Xaa Xaa Xaa Xaa
1               5                   10                  15

Xaa Xaa Xaa Xaa Xaa Xaa Xaa Xaa Xaa His Thr Ala Arg Asn Cys
                20              25              30
```

Arg

```
<210> SEQ ID NO 7
<211> LENGTH: 34
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (10)..(29)
<223> OTHER INFORMATION: "Xaa" at positions 10 to 29 can be any 4 to 20
      random amino acids

<400> SEQUENCE: 7

Met Asn Pro Asn Cys Ala Arg Cys Gly Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Lys Ala
            20                  25                  30

Cys Phe

<210> SEQ ID NO 8
<211> LENGTH: 7
<212> TYPE: PRT
<213> ORGANISM: Artificial sequence
<220> FEATURE:
<223> OTHER INFORMATION: dimerization sequence

<400> SEQUENCE: 8

Glu Phe Leu Ile Val Lys Ser
1               5

<210> SEQ ID NO 9
<211> LENGTH: 9
<212> TYPE: PRT
<213> ORGANISM: Artificial sequence
<220> FEATURE:
<223> OTHER INFORMATION: dimerization sequence

<400> SEQUENCE: 9

Glu Glu Phe Leu Ile Val Lys Lys Ser
1               5

<210> SEQ ID NO 10
<211> LENGTH: 7
<212> TYPE: PRT
<213> ORGANISM: Artificial sequence
<220> FEATURE:
<223> OTHER INFORMATION: dimerization sequence

<400> SEQUENCE: 10

Phe Glu Ser Ile Lys Leu Val
1               5

<210> SEQ ID NO 11
<211> LENGTH: 7
<212> TYPE: PRT
<213> ORGANISM: Artificial sequence
<220> FEATURE:
<223> OTHER INFORMATION: dimerization sequence

<400> SEQUENCE: 11

Val Ser Ile Lys Phe Glu Leu
1               5
```

```
<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 6
<212> TYPE: PRT
<213> ORGANISM: Homo sapiens

<400> SEQUENCE: 13

Ala Arg Arg Arg Arg Pro
1               5

<210> SEQ ID NO 14
<211> LENGTH: 10
<212> TYPE: PRT
<213> ORGANISM: Mus musculus

<400> SEQUENCE: 14

Glu Glu Val Gln Arg Lys Arg Gln Lys Leu
1               5                   10

<210> SEQ ID NO 15
<211> LENGTH: 9
<212> TYPE: PRT
<213> ORGANISM: Mus musculus

<400> SEQUENCE: 15

Glu Glu Lys Arg Lys Arg Thr Tyr Glu
1               5

<210> SEQ ID NO 16
<211> LENGTH: 20
<212> TYPE: PRT
<213> ORGANISM: Xenopus laevis

<400> SEQUENCE: 16

Ala Val Lys Arg Pro Ala Ala Thr Lys Lys Ala Gly Gln Ala Lys Lys
1               5                   10                  15

Lys Lys Leu Asp
            20

<210> SEQ ID NO 17
<211> LENGTH: 31
<212> TYPE: PRT
<213> ORGANISM: Mus musculus

<400> SEQUENCE: 17

Met Ala Ser Pro Leu Thr Arg Phe Leu Ser Leu Asn Leu Leu Leu Leu
1               5                   10                  15

Gly Glu Ser Ile Leu Gly Ser Gly Glu Ala Lys Pro Gln Ala Pro
            20                  25                  30

<210> SEQ ID NO 18
<211> LENGTH: 21
<212> TYPE: PRT
<213> ORGANISM: Homo sapiens

<400> SEQUENCE: 18
```

```
Met Ser Ser Phe Gly Tyr Arg Thr Leu Thr Val Ala Leu Phe Thr Leu
1               5                   10                  15

Ile Cys Cys Pro Gly
            20
```

<210> SEQ ID NO 19
<211> LENGTH: 51
<212> TYPE: PRT
<213> ORGANISM: Mus musculus

<400> SEQUENCE: 19

```
Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
                20                  25                  30

Ile Cys Val Ala Leu Leu Ser Leu Ile Ile Thr Leu Ile Cys Tyr
            35                  40                  45

His Ser Arg
        50
```

<210> SEQ ID NO 20
<211> LENGTH: 33
<212> TYPE: PRT
<213> ORGANISM: Homo sapiens

<400> SEQUENCE: 20

```
Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
                20                  25                  30

Arg
```

<210> SEQ ID NO 21
<211> LENGTH: 37
<212> TYPE: PRT
<213> ORGANISM: Rattus sp.

<400> SEQUENCE: 21

```
Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
                20                  25                  30

Met Gly Leu Leu Thr
            35
```

<210> SEQ ID NO 22
<211> LENGTH: 14
<212> TYPE: PRT
<213> ORGANISM: Gallus gallus

<400> SEQUENCE: 22

```
Met Gly Ser Ser Lys Ser Lys Pro Lys Asp Pro Ser Gln Arg
1               5                   10
```

<210> SEQ ID NO 23
<211> LENGTH: 26
<212> TYPE: PRT
<213> ORGANISM: Homo sapiens

<400> SEQUENCE: 23

Leu Leu Gln Arg Leu Phe Ser Arg Gln Asp Cys Cys Gly Asn Cys Ser

```
1               5                  10                 15
Asp Ser Glu Glu Glu Leu Pro Thr Arg Leu
            20                 25

<210> SEQ ID NO 24
<211> LENGTH: 20
<212> TYPE: PRT
<213> ORGANISM: Rattus norvegicus

<400> SEQUENCE: 24

Lys Gln Phe Arg Asn Cys Met Leu Thr Ser Leu Cys Cys Gly Lys Asn
1               5                  10                 15

Pro Leu Gly Asp
            20

<210> SEQ ID NO 25
<211> LENGTH: 19
<212> TYPE: PRT
<213> ORGANISM: Homo sapiens

<400> SEQUENCE: 25

Leu Asn Pro Pro Asp Glu Ser Gly Pro Gly Cys Met Ser Cys Lys Cys
1               5                  10                 15

Val Leu Ser

<210> SEQ ID NO 26
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 26

Lys Phe Glu Arg Gln
1               5

<210> SEQ ID NO 27
<211> LENGTH: 36
<212> TYPE: PRT
<213> ORGANISM: Cricetulus griseus

<400> SEQUENCE: 27

Met Leu Ile Pro Ile Ala Gly Phe Phe Ala Leu Ala Gly Leu Val Leu
1               5                  10                 15

Ile Val Leu Ile Ala Tyr Leu Ile Gly Arg Lys Arg Ser His Ala Gly
            20                 25                 30

Tyr Gln Thr Ile
        35

<210> SEQ ID NO 28
<211> LENGTH: 35
<212> TYPE: PRT
<213> ORGANISM: Homo sapiens

<400> SEQUENCE: 28

Leu Val Pro Ile Ala Val Gly Ala Ala Leu Ala Gly Val Leu Ile Leu
1               5                  10                 15

Val Leu Leu Ala Tyr Phe Ile Gly Leu Lys His His Ala Gly Tyr
            20                 25                 30

Glu Gln Phe
        35
```

-continued

```
<210> SEQ ID NO 29
<211> LENGTH: 27
<212> TYPE: PRT
<213> ORGANISM: Saccharomyces cerevisiae

<400> SEQUENCE: 29

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
            20                  25

<210> SEQ ID NO 30
<211> LENGTH: 25
<212> TYPE: PRT
<213> ORGANISM: Saccharomyces cerevisiae

<400> SEQUENCE: 30

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 31
<211> LENGTH: 64
<212> TYPE: PRT
<213> ORGANISM: Saccharomyces cerevisiae

<400> SEQUENCE: 31

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 32
<211> LENGTH: 41
<212> TYPE: PRT
<213> ORGANISM: Saccharomyces cerevisiae

<400> SEQUENCE: 32

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 33
<211> LENGTH: 4
<212> TYPE: PRT
<213> ORGANISM: Homo sapiens

<400> SEQUENCE: 33

Lys Asp Glu Leu
1

<210> SEQ ID NO 34
<211> LENGTH: 15
```

```
<212> TYPE: PRT
<213> ORGANISM: Unidentified adenovirus

<400> SEQUENCE: 34

Leu Tyr Leu Ser Arg Arg Ser Phe Ile Asp Glu Lys Lys Met Pro
1               5                   10                  15

<210> SEQ ID NO 35
<211> LENGTH: 15
<212> TYPE: PRT
<213> ORGANISM: Homo sapiens

<400> SEQUENCE: 35

Leu Thr Glu Pro Thr Gln Pro Thr Arg Asn Gln Cys Cys Ser Asn
1               5                   10                  15

<210> SEQ ID NO 36
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 36

Arg Thr Ala Leu Gly Asp Ile Gly Asn
1               5

<210> SEQ ID NO 37
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 37

Met Tyr Arg Met Gln Leu Leu Ser Cys Ile Ala Leu Ser Leu Ala Leu
1               5                   10                  15

Val Thr Asn Ser
            20

<210> SEQ ID NO 38
<211> LENGTH: 29
<212> TYPE: PRT
<213> ORGANISM: Homo sapiens

<400> SEQUENCE: 38

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 39
<211> LENGTH: 27
<212> TYPE: PRT
<213> ORGANISM: Homo sapiens

<400> SEQUENCE: 39

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 40
<211> LENGTH: 18
```

```
<212> TYPE: PRT
<213> ORGANISM: Influenza virus

<400> SEQUENCE: 40

Met Lys Ala Lys Leu Leu Val Leu Leu Tyr Ala Phe Val Ala Gly Asp
1               5                   10                  15

Gln Ile

<210> SEQ ID NO 41
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 41

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 42
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3-6 can be at least 4 of
      any amino acids

<400> SEQUENCE: 42

Met Gly Xaa Xaa Xaa Xaa Gly Gly Pro Pro
1               5                   10

<210> SEQ ID NO 43
<211> LENGTH: 5
<212> TYPE: PRT
<213> ORGANISM: Artificial sequence
<220> FEATURE:
<223> OTHER INFORMATION: linker consensus sequence

<400> SEQUENCE: 43

Gly Ser Gly Gly Ser
1               5

<210> SEQ ID NO 44
<211> LENGTH: 4
<212> TYPE: PRT
<213> ORGANISM: Artificial sequence
<220> FEATURE:
<223> OTHER INFORMATION: linker consensus sequence

<400> SEQUENCE: 44

Gly Gly Gly Ser
1

<210> SEQ ID NO 45
<211> LENGTH: 9
<212> TYPE: PRT
<213> ORGANISM: Unknown
<220> FEATURE:
<223> OTHER INFORMATION: cyclin A destruction box

<400> SEQUENCE: 45
```

-continued

```
Arg Thr Val Leu Gly Val Ile Gly Asp
1               5

<210> SEQ ID NO 46
<211> LENGTH: 27
<212> TYPE: PRT
<213> ORGANISM: Rattus sp.

<400> SEQUENCE: 46

Tyr Met Thr Val Ser Ile Ile Asp Arg Phe Met Gln Asp Ser Cys Val
1               5                   10                  15

Pro Lys Lys Met Leu Gln Leu Val Gly Val Thr
            20                  25

<210> SEQ ID NO 47
<211> LENGTH: 28
<212> TYPE: PRT
<213> ORGANISM: Mus sp.

<400> SEQUENCE: 47

Lys Phe Arg Leu Leu Gln Glu Thr Met Tyr Met Thr Val Ser Ile Ile
1               5                   10                  15

Asp Arg Phe Met Gln Asn Ser Cys Val Pro Lys Lys
            20                  25

<210> SEQ ID NO 48
<211> LENGTH: 27
<212> TYPE: PRT
<213> ORGANISM: Mus sp.

<400> SEQUENCE: 48

Arg Ala Ile Leu Ile Asp Trp Leu Ile Gln Val Gln Met Lys Phe Arg
1               5                   10                  15

Leu Leu Gln Glu Thr Met Tyr Met Thr Val Ser
            20                  25

<210> SEQ ID NO 49
<211> LENGTH: 27
<212> TYPE: PRT
<213> ORGANISM: Mus sp.

<400> SEQUENCE: 49

Asp Arg Phe Leu Gln Ala Gln Leu Val Cys Arg Lys Lys Leu Gln Val
1               5                   10                  15

Val Gly Ile Thr Ala Leu Leu Leu Ala Ser Lys
            20                  25

<210> SEQ ID NO 50
<211> LENGTH: 18
<212> TYPE: PRT
<213> ORGANISM: Mus sp.

<400> SEQUENCE: 50

Met Ser Val Leu Arg Gly Lys Leu Gln Leu Val Gly Thr Ala Ala Met
1               5                   10                  15

Leu Leu

<210> SEQ ID NO 51
<211> LENGTH: 16
<212> TYPE: PRT
<213> ORGANISM: Physalia utriculus
```

```
<400> SEQUENCE: 51

Ala Leu Pro Gly Ala Ile Gly Lys Leu Gly Leu Ala Gly Leu Gln Gly
1               5                   10                  15

<210> SEQ ID NO 52
<211> LENGTH: 16
<212> TYPE: PRT
<213> ORGANISM: Physalia utriculus

<400> SEQUENCE: 52

Gly Leu Asp Glu Ser Ala Gly Ile Leu Phe Pro Ser Ile Asn Leu Ile
1               5                   10                  15

<210> SEQ ID NO 53
<211> LENGTH: 16
<212> TYPE: PRT
<213> ORGANISM: Physalia utriculus

<400> SEQUENCE: 53

Gly Leu Asp Gly Ala His Asp Leu Phe Gly Ala Glu Gly Met Ala Val
1               5                   10                  15

<210> SEQ ID NO 54
<211> LENGTH: 16
<212> TYPE: PRT
<213> ORGANISM: Physalia utriculus

<400> SEQUENCE: 54

Ala Pro Asp Gly Asn Pro Gly Lys Val Gly Pro Ser Ile Val Val Gly
1               5                   10                  15

<210> SEQ ID NO 55
<211> LENGTH: 16
<212> TYPE: PRT
<213> ORGANISM: Physalia utriculus

<400> SEQUENCE: 55

Gly Leu Glu Gly Asn Pro Gly Lys Phe Gly Ile Pro Gly Tyr Lys Val
1               5                   10                  15

<210> SEQ ID NO 56
<211> LENGTH: 16
<212> TYPE: PRT
<213> ORGANISM: Physalia utriculus

<400> SEQUENCE: 56

Thr Ile Pro Lys Asp Ala Lys Leu Val Gly Leu Arg Phe Val Thr Val
1               5                   10                  15

<210> SEQ ID NO 57
<211> LENGTH: 16
<212> TYPE: PRT
<213> ORGANISM: Physalia utriculus

<400> SEQUENCE: 57

Thr Leu Asp Asp Asp Leu Gln Leu Asp Val Leu Ile Ile Val Asp Glu
1               5                   10                  15

<210> SEQ ID NO 58
<211> LENGTH: 16
```

```
-continued

<212> TYPE: PRT
<213> ORGANISM: Physalia utriculus

<400> SEQUENCE: 58

Gly Ile Pro Val Asp Phe Lys Phe Ile Gly Lys Arg Ile Gln Asn Gln
1               5                   10                  15
```

PHYSALIA FLUORESCENT PROTEINS

This application claims the benefit of U.S. Provisional Application No. 60/314,378, filed Aug. 22, 2001 (pending), under 35 U.S.C. § 119(e).

This invention was made with United States Government support under Grant No. U54 NS39406 awarded by the National Institutes of Health. The government has certain rights in the invention.

FIELD OF THE INVENTION

This invention relates to the field of fluorescent proteins. In particular, this invention relates to *Physalia* fluorescent proteins (PFPs) and, more particularly, to PFPs of a *Physalia* species, and to methods of detecting and isolating PFPs. The invention further relates to the use of PFPs, including recombinant PFPs, as reporter molecules in in vitro and in vivo biological assays, including screening assays and cellular assays.

BACKGROUND OF THE INVENTION

Photochromic materials, such as fluorescent proteins, can be used in a variety of applications and have particular utility as a tool in molecular biology (see, e.g., Irie, M. & Mori, M. J. Org. Chem. 53:803 (1988); Parthenopoulos, D. A. & Rentzepis, P. M. Science 245:843 (1989); Hanazawa, M., et al. J. Chem. Soc. Chem. Commun. 206 (1992); Dvornikov, A. S., et al. J. Phys. Chem. 98:6746–6752 (1994); Dvornikov, A. S. & Rentzepis, P. M. Opt. Mem. Neur. Netw. 3:75–86 (1994); U.S. Pat. No. 4,471,470; and U.S. Pat. No. 5,325,324). However, the number of known fluorescent proteins is limited.

In general, photochromic materials have two states that can be interconverted by irradiation (see, e.g., U.S. Pat. No. 6,046,925). For example, the fluorescence behavior of wild-type (WT) green fluorescent protein (GFP) is known to have two absorption maxima, one at 395 nm, the other at 465 nm, but only one emission peak at 490 nm, indicating a common excited state (see, e.g., Heim, R., et al. Proc. Nat. Acad. Sci., USA 91:12501 (1994)). These absorption peaks have been attributed to the neutral and anionic fluorophore states, respectively, which can be interconverted by proton transfer between the fluorophore and Glu222 (see, e.g., Cubitt, A. B., et al. Trends in Biochem. Sci. 20:448 (1995); Chattoraj, M., et al. Proc. Nat. Acad. Sci., USA 93, 8362 (1996); and Brejc, K., et al. Proc. Nat. Acad. Sci., USA 94:2306–2311 (1997)). Ser65 and Thr203 are particularly close to the chromophore in GFPs (see, e.g., Ormo, M., et al. Science 273:1392 (1996); Yang, F., et al. Nature Biotech. 14:1246 (1996)). Consequently, these residues can influence the photophysical properties of the protein. Alteration of Ser65 strongly favors ionization of the chromophore by hindering solvation and ionization of Glu222, whereas mutational loss of the Thr203 hydroxyl exerts a weaker opposing effect by reducing the solvation of the anionic form (see, e.g., Ormo, M., et al. Science 273:1392 (1996); Yang, F., et al. Nature Biotech. 14:1246 (1996). Aromatic residues at position 203 of GFP increase the peak excitation wavelength by 13–24 nm, probably by increasing the polarizability around the chromophore through p—p interactions (see, e.g., Ormo, M., et al. Science 273:1392 (1996)).

The fluorescent proteins of various aquatic organisms, such as those in the phylum Cnidaria, act as energy-transfer acceptors in bioluminescence and thereby emit fluorescence (see, e.g., Ward, W. W., et al., Photochem. Photobiol., 35:803–808 (1982); and Levine, L. D., et al., Comp. Biochem. Physiol., 72B:77–85 (1982). GFP proteins have been modified to alter their excitation and emission spectra. Specifically, a variety of GFPs have been constructed by modifying the amino acid sequence of a naturally-occurring (or wild-type) GFP from *Aequorea Victoria* (see, e.g., Prasher, D. C., et al., Gene, 111:229–233 (1992); Heim, R., et al., Proc. Natl. Acad. Sci., USA, 91:12501–04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. Further, the cDNA of GFP can be concatenated with those encoding other proteins; and the resulting fusion polypeptides can be fluorescent and retain the biochemical features of the partner proteins (see, e.g., Cubitt, A. B., et al., Trends in Biochem. Sci. 20:448–455 (1995)). Mutagenesis studies have produced GFP mutants with shifted wavelengths of excitation or emission (see, e.g., Heim, R. & Tsien, R. Y. Current Biol. 6:178–182 (1996); and Tsien, R. Y., et al., Trends Cell Biol. 3:242–245 (1993).

In addition, mutations in *Aequorea* fluorescent proteins, referred to as "folding mutations," improve the ability of fluorescent proteins to fold at higher temperatures and to be more fluorescent when expressed in mammalian cells, but have little or no effect on the peak wavelengths of excitation and emission. Such mutations can be combined with mutations that influence the spectral properties of GFP to produce proteins with altered spectral and folding properties. In addition, new fluorescent proteins based on GFP have been identified by random screening of GFPs (see, for example, Heim, R., et al. Proc. Natl. Acad. Sci. USA 91:12501–12504 (1994); Ehrig, et al. FEBS Lett. 367:163–166 (1995); and Delagrave, et al. Bio/Technology 13:151–154 (1995)).

The utility of fluorescent proteins as a tool in molecular biology has prompted the search for other proteinaceous fluorophores with different and improved properties, as compared to known fluorescent proteins. Thus, there is a need for the isolation and characterization of new fluorescent proteins that exhibit properties not currently available in the limited number of known fluorescent proteins.

Accordingly, an object of the present invention is to provide novel fluorescent proteins for use as a tool in molecular biology. In particular, an object of the present invention is to provide methods and compositions comprising a PFP, including for example a recombinant PFP and, more particularly, a fusion PFP for use in in vitro and in vivo biological assays, including screening assays and cellular assays.

SUMMARY OF THE INVENTION

In accordance with the above objects, the present invention provides *Physalia* fluorescent proteins (PFPs) and, more particularly, PFPs of a *Physalia* species, and methods of detecting and isolating PFPs. Also provided are methods and compositions for using PFPs, including recombinant PFPs, as reporter molecules in in vitro and in vivo biological assays, including screening assays and cellular assays. In addition, the invention provides PFP fusion polypeptides. Examples of *Physalia* species include, but are not limited to *P. utriculus* and *P. physalis*.

In one aspect, the invention provides an isolated PFP characterized by an excitation wavelength in a range of about 210–550 nm.

In another aspect, the invention provides an isolated PFP characterized by an excitation wavelength in a range of about 400–950 nm.

In another aspect, the invention provides an isolated PFP characterized by an emission wavelength in a range of about 400–950 nm, when the PFP is excited at a wavelength in a range of about 210–550 nm.

In another aspect, the invention provides an isolated PFP characterized by an emission wavelength of about 456 nm, when the PFP is excited at an excitation wavelength of 221 nm.

In another aspect, the invention provides an isolated PFP characterized by an emission wavelength of about 421 nm, when the PFP is excited at an excitation wavelength of 222 nm.

In another aspect, the invention provides an isolated PFP characterized by an emission wavelength of about 600 nm when the PFP excited at an excitation wavelength of 222 nm.

In another aspect, the invention provides an isolated PFP characterized by an emission wavelength of about 597 nm, when the PFP is excited at an excitation wavelength of 301 nm.

In another aspect, the invention provides an isolated PFP characterized by an emission wavelength of about 598 nm, when the PFP is excited at an excitation wavelength of 301 nm.

In another aspect, the invention provides an isolated PFP characterized by an emission wavelength of about 600 nm when when the PFP is excited at an excitation wavelength of 301 nm.

In another aspect, the invention provides an isolated PFP characterized by an emission wavelength in a range of about 888–898 nm, when the PFP is excited at an excitation wavelength of 301 nm.

In another aspect, the invention provides an isolated PFP characterized by an emission wavelength of about 888 nm, when the PFP is excited at an excitation wavelength of 301 nm.

In another aspect, the invention provides an isolated PFP characterized by an emission wavelength of about 838 nm, when the PFP is excited at an excitation wavelength of 421 nm.

In another aspect, the invention provides an isolated PFP characterized by an emission wavelength of about 900 nm, when the PFP is excited at an excitation wavelength of 450 nm.

In another aspect, the invention provides an isolated PFP characterized by an emission wavelength of about 898 nm, when the PFP is excited at an excitation wavelength of 451 nm.

In an additional aspect, a PFP of the present invention is further characterized by a molecular weight of about 10–15 kDa. Also, in an additional aspect, a PFP of the present invention is further characterized by a molecular weight of about 35–40 kDa. In a further aspect, a PFP of the present invention is of the species *P. utriculus*.

In another aspect, the invention provides a method for detecting a PFP, the method comprising: a) providing a sample comprising a PFP; b) applying to the sample a light source having an excitation wavelength in the range of about 210–550 nm; and c) detecting an emission wavelength in a range of about 400–950 nm, wherein the emission wavelength is indicative of the PFP.

In another aspect, the invention provides a method for detecting a PFP, the method comprising:
a) providing a sample comprising a PFP; b) applying a light source having an excitation wavelength within the excitation spectrum of the PFP, thereby exciting the PFP; and c) detecting an emission wavelength selected from a group of emission wavelengths consisting of: an emission wavelength of about 456 nm, when the PFP is excited by an excitation wavelength of 221 nm; an emission wavelength of about 421 nm, when the PFP is excited by an excitation wavelength of 222 nm; an emission wavelength of about 600 nm, when the PFP is excited by an excitation wavelength of 222 nm; an emission wavelength of about 597 nm, when the PFP is excited by an excitation wavelength of 301 nm; an emission wavelength of about 598 nm, when the PFP is excited by an excitation wavelength of 301 nm; an emission wavelength of about 600 nm, when the PFP is excited by an excitation wavelength of 301 nm; an emission wavelength in a range of about 888–898 nm, when the PFP is excited by an excitation wavelength of 301 nm; an emission wavelength of about 888 nm, when the PFP is excited by an excitation wavelength of 301 nm; an emission wavelength of about 838 nm, when the PFP is excited by an excitation wavelength of 421 nm; an emission wavelength of about 900 nm, when the PFP is excited by an excitation wavelength of 450 nm; and an emission wavelength of about 898 nm, when the PFP is excited by an excitation wavelength of 451 nm, wherein the emission wavelength is indicative of the PFP.

In another aspect, the invention provides a method for isolating a PFP, the method comprising:
a) providing a sample comprising a PFP; b) applying to the sample a light source having an excitation wavelength in the range of about 210–550 nm; c) detecting an emission wavelength in a range of about 400–950 nm, wherein the emission wavelength is indicative of the PFP; and d) selecting the PFP based on the emission wavelength.

In another aspect, the invention provides a method for isolating a PFP, the method comprising:
a) providing a sample comprising a PFP; b) applying a light source having an excitation wavelength within the excitation spectrum of the PFP, thereby exciting the PFP; and c) detecting an emission wavelength selected from a group of emission wavelengths consisting of: an emission wavelength of about 456 nm, when the PFP is excited by an excitation wavelength of 221 nm; an emission wavelength of about 421 nm, when the PFP is excited by an excitation wavelength of 222 nm; an emission wavelength of about 600 nm, when the PFP is excited by an excitation wavelength of 222 nm; an emission wavelength of about 597 nm, when the PFP is excited by an excitation wavelength of 301 nm; an emission wavelength of about 598 nm, when the PFP is excited by an excitation wavelength of 301 nm; an emission wavelength of about 600 nm, when the PFP is excited by an excitation wavelength of 301 nm; an emission wavelength in a range of about 888–898 nm, when the PFP is excited by an excitation wavelength of 301 nm; an emission wavelength of about 888 nm, when the PFP is excited by an excitation wavelength of 301 nm; an emission wavelength of about 838 nm, when the PFP is excited by an excitation wavelength of 421 nm; an emission wavelength of about 900 nm, when the PFP is excited by an excitation wavelength of 450 nm; and an emission wavelength of about 898 nm, when the PFP is excited by an excitation wavelength of 451 nm, wherein the emission wavelength is indicative of the PFP; and d) selecting the PFP based on the emission wavelength.

In an additional aspect, the methods further comprise detecting the molecular weight of the protein, wherein the molecular weight is about 10–15 kD. In an additional aspect, the methods further comprise detecting the molecular weight of the protein, wherein the molecular weight is about 35–40 kD. In an additional aspect, the methods comprise detecting a PFP of the species *P. utriculus*.

DETAILED DESCRIPTION OF THE FIGURES

FIG. 1 depicts a sample of tentacle from *P. utriculus* using light microscopy.

FIG. 2 depicts the fluorescent activity from a sample of tentacle from *P. utriculus* using fluorescent microscopy.

FIG. 3 depicts two fluorescent *P. utriculus* protein gel bands resolved at approximately 12 kD and at approximately 37 kD, using polyacrylamide gel electrophoresis (PAGE). The fluorescent activity of the PFPs resolved at 12 kD and 37 kD is detected using fluorescent microscopy in the native polyacrylamide gel and not in the denaturing polyacrylamide gel.

FIG. 4 depicts an emission scan of PFP from a sample prepared from a tentacle of *P. utriculus*. In FIG. 4A PFP from the sample is excited at an excitation wavelength of 300 nm. In FIG. 4B PFP from a 1:500 dilution of the sample is excited at an excitation wavelength of 300 nm.

FIG. 5 depicts a excitation scans of PFP from a sample prepared from a tentacle of *P. utriculus* examined for emissions at 600 nm (FIG. 5A) and at 898 nm (FIG. 5B). "Ex" is excitation and "Em" is emission.

FIG. 6 shows a summary of the excitation and emission spectra of PFP from a sample prepared from a tentacle of *P. utriculus*. "Ex" is excitation and "Em" is emission.

DETAILED DESCRIPTION OF THE INVENTION

The technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entirety as though set forth in full. Standard reference works setting forth the general principles of recombinant DNA technology include Sambrook, J., et al., Molecular Cloning,: A Laboratory Manual, 2d Ed., Cold Spring Harbor Laboratory Press, Planview, N.Y. (1989); McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted. It is believed that one skilled in the art can, based on the description herein, utilize the present invention to its fullest extent. All patents and publications cited herein are hereby incorporated by reference.

The present invention provides *Physalia* fluorescent proteins (PFPs) and, more particularly, PFPs of a *Physalia* species, and methods of detecting and isolating PFPs. Also provided are methods and compositions for using PFPs as reporter molecules in in vitro and in vivo biological assays, including screening assays and cellular assays. In a preferred embodiment, the PFP is a recombinant PFP and, more preferably, the PFP is a fusion polypeptide. Examples of *Physalia* species include, but are not limited to, *P. utticulus* and *P. physalis*. In a preferred embodiment, the PFP is of the species *P. utriculus*.

The advantages of the present invention include novel fluorescent proteins having an excitation wavelength within an unprecedented broad band-width of the excitation spectrum, as compared to known fluorescent proteins. For example, in some embodiments, the PFPs of the present invention have an excitation wavelength within a range from about 210–550 nm. More specifically, the PFPs of the present invention exhibit several unique and valuable properties which include, but are not limited to: 1) a dramatic excitation emission wavelength set of 301 nm excitation and 598 nm emission; 2) excitation emission wavelength sets that overlap and span from 220 nm to 898 nm; and far-red emission resulting from an excitation wavelength of 456 nm and 301 nm. The 898 nm emission peak is unprecented as compared to other known fluorescent proteins. The highest wavelength emission of a known fluorescent protein has an emission wavelength of 716 nm with excitation wavelength at 414 nm (see, e.g., emission spectra at the Web page at RH-414 Bio-Rad fluorescence.bio-rad.com; the information in the Web page is incorporated herein in its entirety).

In a preferred embodiment, a PFP of the present invention functions as a universal reporter molecule. In another preferred embodiment, a PFP of the present invention has an intense red-shifted emission in a range that is distinguished from the emission ranges of known fluorophores. In another preferred embodiment, the emission range of a PFP of the present invention is uniquely outside of emission ranges for known fluorophores and, thus, is not affected by interference from the overlapping emission spectra from such fluorophores. Thus, the PFPs of the present invention are particularly useful in biological assays or reactions where multiple and different fluorophores are used. Further, PFPs of the present invention provide a unique opportunity to study complex fluorescence energy transfer reactions, for example, energy transfer reactions that occur in protein-protein interactions. Thus, the discovery of the fluorescent proteins of the present invention, and their use in the methods and compositions of the present invention, represent an advancement in the art Accordingly, the present invention further provides methods and compositions that exploit the autofluorescent properties of the isolated PFPs of the present invention. These methods include, but are not limited to, the use of PFPs as reporter molecules in cell screening assays, including intracellular assays; the use of PFPs as scaffold proteins for fusions with random peptide libraries. Similarly, compositions of PFPs are provided, including constructs of PFPs such as fusion constructs that include a PFP as a reporter gene, and retroviral constructs including a PFP and internal ribosome entry sites (IRES). The invention provides uses for PFPs, similar to those described for Green fluorescent protein in WO 95/07463, hereby incorporated by reference, in its entirety.

This invention is directed most generally to novel fluorescent proteins of the genus *Physalia* designated PFPs. In a preferred embodiment, a PFP of the present invention is from a *Physalia* species. Examples of *Physalia* species include, but are not limited to, *P. physalis* and *P. utriculus*. In a preferred embodiment, the *Physalia* species is *P. utriculus*.

*Physalia* is a pelagic animal (or organism) and, thus, samples of *Physalia* can be collected from ocean waters. In a preferred embodiment, the samples are of juvenile *Physa-*

*lia*. In another peferred embodiment, the samples are of adult *Physalia*. In some preferred embodiments, the sample is from a tentacle of *Physalia*. In another preferred embodiment, the samples are of a Physali species, e.g., *P. physalis* or *P. utriculus*. In some embodiments, frozen or preserved samples are used. In a preferred embodiment, fresh samples are used.

Naturally-occuring or Wild-type (WT) PFPs can be mutated to produce new proteins and protein fragments that are photochromic. A photochromic fluorescent protein is a protein that has more than one stable state having different spectral properties (see, e.g., U.S. Pat. No. 6,046,925, hereby incorporated by reference in its entirety). Each state has excitation or emission spectra that are shifted from one wavelength region to another wavelength region in the two states. A photochromic material switches between states by irradiation with light of appropriate wavelengths. The switching between states can be reversible. The two states are preferably stable at room temperature and in the dark.

The degree of photochromism can be determined by any change in spectral characteristic of the fluorescent protein. Preferably, photochromic behavior can be identified by monitoring changes in the excitation spectrum, which are determined as a function of the change in the ratio of excitation intensities from the different states of the photochromic fluorescent protein at a particular wavelength. A more detailed analysis of the photochromism can be accomplished by monitoring the change in the excitation intensity at more than one wavelength.

For example, the photochromic fluorescent protein can be excited by light of appropriate intensity within the excitation spectrum of the fluorophore in one state. The excited state fluorophore emits energy as fluorescent light. The photochromic fluorescent protein can be switched to a different or second stable state by further irradiation and this second stable state can then be excited by light at a different or second excitation wavelength.

In a preferred embodiment the photochromic fluorescent protein has a high fluorescence quantum yield and a high degree of reversibility of the photoconversion between states.

Fluorescence in a sample can be measured using, for example, a fluorometer. In general, excitation radiation, from an excitation source having a first wavelength, passes through excitation optics. The excitation optics cause the excitation radiation to excite the sample. In response, fluorophores in the sample emit radiation which has a wavelength that is different from the excitation wavelength. Collection optics then collect the emission from the sample. The device can include a temperature controller to maintain the sample at a specific temperature while it is being scanned. The device can also include a multi-axis translation stage moves a microtiter plate holding a plurality of samples in order to position different wells to be exposed. The multi-axis translation stage, temperature controller, autofocusing feature, and electronics associated with imaging and data collection can be managed by an appropriately programmed digital computer. The computer also can transform the data collected during the assay into another format for presentation.

Methods of determining the properties of fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y. L., San Diego: Academic Press (1989), pp. 219–243; Turro, N. J., Modern Molecular Photochemistry, Menlo Park: Benjamin Cummings Publishing Co. (1978), pp. 296–361. The excited state lifetime and quantum yields can be determined using methods known in the art (see, e.g., J. N. Miller, ed., Standards in Fluorescence Spectrometry, New York: Chapman and Hall (1981).

For example, the fluorescent activity of PFPs can be detected using light or fluorescent microscopy (using, e.g., Zeiss Axiophot, Nikon Microphot FXA, and Olympus BH2-RFC and BX50 equipped for epifluorescence microscopy). Filter sets for fluorescein isothiocyanate fluorescence can be used (for example, the Zeiss filter set used a BP450–490 excitation filter, 510 nm dichroic, and either a BP515–565 or a LP520 emission filter). In addition, filter sets that excite at lower wavelengths can be used (for example, a Zeiss filter set with BP395–440 and LP470 filters and a 460 nm dichroic or with BP340–390 and LP400 filters with a 395 nm dichroic). In some instances a xenon lamp or mercury lamp can be used. Further, the fluorescence signal can be enhanced by methods known in the art, e.g., by using low intensity light cameras. In addition, Fluorescent cell sorting devices, for example a Fluorescent Activated Cell Sorting (FACS) can be used to detect the fluoresent proteins of the present invention.

In preferred embodiments, a PFP of the present invention has distinguishing fluorescence activities which include, but are not limited to, an excitation wavelength in a range from about 210 nm to about 550 nm. More specifically, PFPs of the present invention exhibit unique and valuable properties which include, but are not limited to: a dramatic 301 nm excitation wavelength and a 598 nm emission wavelength; or excitation emission sets that overlap and span from 220 nm to 898 nm; or a far red emission results from excitation at 456 nm and at 301 nm. The 898 nm emission peak is especially noteworthy in view of the fact that no other fluorescent protein has been identified with a red-shifted emission within this wavelength. In contrast, the highest wavelength emission of a known fluorescent protein has an emission wavelength of 716 nm with excitation at 414 nm (see, e.g., emission spectra at the Web page at RH-414 Bio-Rad fluorescence.bio-rad.com; the information in the Web page is incorporated herein in its entirety).

Thus, based on the characteristic or unique fluorescent properties of PFPs, novel PFPs can be identified and isolated. More specifically, novel PFPs can be detected, selected, and isolated based on a fluorescent property that is characteristic or unique to a PFP as described herein. For example, novel PFPs can be identified by random screening of expression libraries (see, e.g., Heim, R., et al. Proc. Natl. Acad. Sci. USA 91:12501–12504 (1994); Ehrig, et al. FEBS Lett. 367:163–166 (1995); and Delagrave, et al. Biotechnology 13:151–154 (1995)).

Accordingly, in a preferred embodiment, a PFP of the present invention is characterized by an excitation wavelength preferably in a range of about 210–550 nm, and more preferably about 220–500 nm. In another preferred embodiment, a PFP of the present invention is characterized by an emission wavelength preferably in a range of about 200–990 nm, preferably 350–950, and more preferably about 400–900 nm.

In another preferred embodiment, a PFP of the present invention is characterized by an emission wavelength in a range of about 400–950 nm, when the PFP is excited at a wavelength in a range of about 210–550 nm.

In another preferred embodiment, a PFP of the present invention is characterized by an emission wavelength of about 456 nm when excited at an excitation wavelength of 221 nm.

In another preferred embodiment, a PFP of the present invention is characterized by an emission wavelength of about 421 nm when excited at an excitation wavelength of 222 nm. In another preferred embodiment, a PFP of the present invention is characterized by an emission wavelength of about 600 nm when excited at an excitation wavelength of 222 nm. In another preferred embodiment, a PFP of the present invention is characterized by an emission wavelength of about 597 nm when excited at an excitation wavelength of 301 nm. In another preferred embodiment, a PFP of the present invention is characterized by an emission wavelength of about 598 nm when excited at an excitation wavelength of 301 nm. In another preferred embodiment, a PFP of the present invention is characterized by an emission wavelength of about 600 nm when excited at an excitation wavelength of 301 nm. In another preferred embodiment, a PFP of the present invention is characterized by an emission wavelength in a range of about 888–898 nm when excited at an excitation wavelength of 301 nm. In another preferred embodiment, a PFP of the present invention is characterized by an emission wavelength of about 888 nm when excited at an excitation wavelength of 301 nm. In another preferred embodiment, a PFP of the present invention is characterized by an emission wavelength of about 838 nm when excited at an excitation wavelength of 421 nm. In another preferred embodiment, a PFP of the present invention is characterized by an emission wavelength of about 900 nm when excited at an excitation wavelength of 450 nm. In another preferred embodiment, a PFP of the present invention is characterized by an emission wavelength of about 898 nm when excited at an excitation wavelength of 451 nm.

In an additional embodiment, a PFP of the present invention is further characterized by a molecular weight of about 10–15 kDa. Also, in an additional embodiment, a PFP of the present invention is further characterized by a molecular weight of about 35–40 kDa. In another embodiment, a PFP of the present invention is of the species *P. utriculus*.

In another preferred embodiment, the invention provides a method for detecting a PFP, the method comprising: a) providing a sample comprising a PFP; b) applying to the sample a light source having an excitation wavelength in the range of about 210–550 nm; and c) detecting an emission wavelength in a range of about 400–950 nm, wherein the emission wavelength is indicative of the PFP.

In another preferred embodiment, the invention provides a method for detecting a PFP, the method comprising: a) providing a sample comprising a PFP; b) applying a light source having an excitation wavelength within the excitation spectrum of PFP, thereby exciting the PFP; and c) detecting an emission wavelength selected from a group of emission wavelengths consisting of: an emission wavelength of about 456 nm, when the PFP is excited by an excitation wavelength of 221 nm; an emission wavelength of about 421 nm, when the PFP is excited by an excitation wavelength of 222 nm; an emission wavelength of about 600 nm, when the PFP is excited by an excitation wavelength of 222 nm; an emission wavelength of about 597 nm, when the PFP is excited by an excitation wavelength of 301 nm; an emssion wavelength of about 598 nm, when the PFP is excited by an excitation wavelength of 301 nm; an emission wavelength of about 600 nm, when the PFP is excited by an excitation wavelength of 301 nm; an emission wavelength in a range of about 888–898 nm, when the PFP is excited by an excitation wavelength of 301 nm; an emission wavelength of about 888 nm, when the PFP is excited by an excitation wavelength of 301 nm; an emission wavelength of about 838 nm, when the PFP is excited by an excitation wavelength of 421 nm; an emission wavelength of about 900 nm, when the PFP is excited by an excitation wavelength of 450 nm; and an emission wavelength of about 898 nm, when the PFP is excited by an excitation wavelength of 451 nm, wherein the emission wavelength is indicative of the PFP.

In another preferred embodiment, the invention provides a method for isolating a PFP, the method comprising: a) providing a sample comprising a PFP; b) applying to the sample a light source having an excitation wavelength in the range of about 210–550 nm; c) detecting an emission wavelength in a range of about 400–950 nm, wherein the emission wavelength is indicative of the PFP; and d) selecting the PFP based on the emission wavelength.

In another preferred embodiment, the invention provides a method for isolating a PFP, the method comprising: a) providing a sample comprising a PFP; b) applying a light source having an excitation wavelength within the excitation spectrum of the PFP, thereby exciting the PFP; and c) detecting an emission wavelength selected from a group of emission wavelengths consisting of: an emission wavelength of about 456 nm, when the PFP is excited by an excitation wavelength of 221 nm; an emission wavelength of about 421 nm, when the PFP is excited by an excitation wavelength of 222 nm; an emission wavelength of about 600 nm, when the PFP is excited by an excitation wavelength of 222 nm; an emission wavelength of about 597 nm, when the PFP is excited by an excitation wavelength of 301 nm; an emission wavelength of about 598 nm, when the PFP is excited by an excitation wavelength of 301 nm; an emission wavelength of about 600 nm, when the PFP is excited by an excitation wavelength of 301 nm; an emission wavelength in a range of about 888–898 nm, when the PFP is excited by an excitation wavelength of 301 nm; an emission wavelength of about 888 nm, when the PFP is excited by an excitation wavelength of 301 nm; an emission wavelength of about 838 nm, when the PFP is excited by an excitation wavelength of 421 nm; an emission wavelength of about 900 nm, when the PFP is excited by an excitation wavelength of 450 nm; and an emission wavelength of about 898 nm, when the PFP is excited by an excitation wavelength of 451 nm, wherein the emission wavelength is indicative of the PFP; and d) selecting the PFP based on the emission wavelength.

In an additional embodiment, the methods further comprise detecting the molecular weight of the protein, wherein the molecular weight is about 10–15 kD. In an additional embodiment, the methods further comprises detecting the molecular weight of the protein, wherein the molecular weight is about 35–40 kD. In an additional embodiment, the methods further comprise detecting a PFP of the species *P. utriculus*.

In addition, based on a sequence of a known PFP, novel PFPs can be identified by random screening of expression libraries based on excitation and emission spectra. For example, bacteria can be transformed with PFP cDNA (containing a large number of different mutations) and spread onto agar plates following standard molecular biological methods such as described in Chapter 1 of Molecular Cloning, a Laboratory Manual, 2nd ed., by J Sambrook, E. F. Fritsch & T. Maniatis, Cold Spring Harbor Laboratory Press (1989). The resulting bacterial colonies can be illuminated with different wavelengths and the emission spectra obtained. Based on the excitation and emission spectra, positive colonies can then be selected and further cultured.

This procedure can be carried out, for example, by eye or by a digital imaging system on a computer (see, e.g., Youvan, D. C., etal. Methods in Enzymology, 246:732–748 (1995)).

In a preferred embodiment, a PFP of the present invention is isolated by collecting fresh samples of Physalia , preferably Physalia utriculus; preparing a protein extract from the sample, preferably a tentacle of Physalia ; fractionating the proteins in the extract based on fluorescent activity and, optionally, another property of the proteins, e.g., molecular weight; isolating the fluorescent proteins; and purifying, sequencing and cloning the proteins. This approach can be performed using methods well known in the art.

In another preferred embodiment, a PFP of the present invention is isolated by collecting fresh samples of Physalia , preferably Physalia utriculus; and preparing an expression library from the sample. The expression products of the library can then be screened for fluorescent activity, or can be screened for sequences homologous to known PFPs.

PFPs can be produced, for example, as components of fusion polypeptides using recombinant DNA technology (see, e.g., U.S. patent Ser. No. 08/706,408). Recombinant production of PFPs involve expressing nucleic acids having sequences that encode such proteins. Nucleic acids encoding PFP fusion polypeptides can be obtained by methods known in the art. For example, a nucleic acid encoding a PFP can be isolated using the polymerase chain reaction (PCR) on cDNA prepared from Physalia RNA using primers based on the DNA sequence of known PFP. PCR methods are described in, e.g., U.S. patent Ser. No. 4,683,195; and Mullis, et al. Cold Spring Harbor Symp. Quant. Biol. 51:263 (1987), and Erlich, ed., PCR Technology, (Stockton Press, NY, 1989). The nucleic acid can encode a fusion polypeptide in which a single polypeptide includes the PFP within a longer polypeptide.

Mutant versions of PFPs can be made by site-specific mutagenesis of other nucleic acids encoding a PFP, or by random mutagenesis caused by increasing the error rate of the PCR of the original PCP polynucleotide with, e.g., 0.1 mM $MnCl_2$ and unbalanced nucleotide concentrations.

In one embodiment, the mutated PFPs of the present invention are "folding mutations." Such mutations can improve the ability of PFPs to fold at higher temperatures and to be more fluorescent when expressed in cells (preferably, mammalian cells). In preferred embodiments, such mutations have little or no effect on the peak wavelengths of excitation and emission. Such mutations may be combined with mutations that influence the spectral properties of a PFP to produce proteins with altered spectral and folding properties.

The construction of expression vectors and the expression of genes in transfected cells involves the use of molecular cloning techniques also well known in the art. Sambrook et al., Molecular Cloning-A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing coding sequence of a PFP and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Transformation of a host cell with recombinant DNA may be carried out by conventional techniques as are well known to those skilled in the art. Where the host is prokaryotic, such as I, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see, e.g., Eukaryotic Viral Vectors, Cold Spring Harbor Laboratory, Gluzman ed., 1982)). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A variety of host-expression vector systems may be utilized to express a PFP coding sequence. Examples of these host-expression vector systems include, but are not limited: bacteria transformed with recombinant bacteriophage DNA, plasmid DNA or cosmid DNA expression vectors containing a fluorescent protein coding sequence; yeast transformed with recombinant yeast expression vectors containing the fluorescent protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a PFP coding sequence; insect cell systems infected with recombinant virus expression vectors (e.g., baculovirus) containing a fluorescent protein coding sequence; or animal cell systems infected with recombinant virus expression vectors (e.g., retroviruses, adenovirus, vaccinia virus) containing a fluorescent protein coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544; 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted photochromic fluorescent protein coding sequence.

In bacterial systems a number of expression vectors may be advantageously selected depending upon the use intended for the photochromic fluorescent protein expressed. For example, when large quantities of the photochromic fluorescent protein are to be produced, vectors which direct the expression of high levels of fusion protein products that are readily purified may be desirable. Those which are engineered to contain a cleavage site to aid in recovering PFPs are preferred.

In yeast, a number of vectors containing constitutive or inducible promoters may be used. For review see, Current Protocols in Molecular Biology, Vol 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. 11, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D. M. Glover, IRL Press, Wash., D.C., 1986). Alternatively, vectors may be used which promote integration of foreign DNA sequences into the yeast chromosome.

In cases where plant expression vectors are used, the expression of a photochromic fluorescent protein coding sequence may be driven by any of a number of promoters. For example, viral promoters such as the 35S RNA and 19S RNA promoters of CaMV (Brisson, et al., Nature 310:511–514, 1984), or the coat protein promoter to TMV (Takamatsu, et al., EMBO J. 6:307–311, 1987) may be used; alternatively, plant promoters such as the small subunit of RUBISCO (Coruzzi, et al., 1984, EMBO J. 3:1671–1680; Broglie, et al., Science 224:838–843, 1984); or heat shock promoters, e.g., soybean hsp17.5-E or hsp7.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421–463, 1988; and Grierson & Corey, Plant Molecular Biology, 2d Ed., Blackie, London, Ch. 7–9, 1988.

An alternative expression system which could be used to express a PFP is an insect system. In one such system, *Autographa californica* nuclear polyhedrosis virus (AcNPV) is used as a vector to express foreign genes. The virus grows in *Spodoptera frugiperda* cells. A PFP coding sequence may be cloned into non-essential regions (for example, the polyhedrin gene) of the virus and placed under control of an AcNPV promoter (for example the polyhedrin promoter).

Successful insertion of the photochromic fluorescent protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see e.g., Smith, etal., J. Viol. 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of a PFP. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the photochromic fluorescent protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the photochromic fluorescent protein in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA,79:7415–7419, 1982; Mackett, et al., J. Virol. 49:857–864, 1984; Panicali, et al., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the photochromic fluorescent protein gene in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the photochromic fluorescent protein cDNA controlled by appropriate expression control elements (e.g., promoter, enhancer, sequences, transcription terminators, poly-adenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in $tk^{31}$, hgprt or aprt cells respectively.

Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

DNA sequences encoding the PFP of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

Recombinant PFPs can be produced by expression of nucleic acid encoding the protein in prokaryotes, such as E. coli or in eukaryotes, such as yeast cells or mammalian cells.

PFP constructs can also contain a tag to simplify isolation of a PFP. For example, a polyhistidine tag of, e.g., six histidine residues, can be incorporated at the amino terminal end of a PFP. The polyhistidine tag allows convenient isolation of the protein in a single step by nickel-chelate chromatography.

In a preferred embodiment, a PFP of the present invention is a fusion protein produced by recombinant DNA technology. The invention also envisions PFP fusion proteins that contain extra amino acid sequences at the amino and/or carboxy termini, for example, polyhistidine tags.

Thus, PFPs encoded by a recombinant nucleic acid include sequences coding for expression the protein. The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify a PFP fusion polypeptide. E. coli is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

Recombinant PFPs can be expressed in E. coli in large scale for in vitro assays. Purification from bacteria is simplified when the sequences include polyhistidine tags for one-step purification by nickel-chelate chromatography. Alternatively, the substrates can be expressed directly in a desired host cell for assays in situ.

In a preferred embodiment a PFP of the present invention is partially purified and more preferably, purified. However, a PFP of the present invention may be used without purification, for example, in a crude protein extract, cell, tissue, or organism.

The PFPs of the present invention can be used, for example, in applications involving fluorescence resonance energy transfer (FRET). Such applications can detect events as a function of the movement of fluorescent donors and acceptor towards or away from each other. One or both of the donor/acceptor pair can be a fluorescent protein. The efficiency of FRET depends on the separation distance and the orientation of the donor and acceptor fluorescent protein moieties (see, e.g., Forster, T. Ann. Physik 2:55–75 (1948); and Energy transfer parameters of aromatic compounds, Academic Press, New York and London (1973). FRET is a nondestructive spectroscopic method that can monitor proximity and relative angular orientation of fluorophores in living cells. See, for example, Adams, S. R., et al., Nature 349:694–697 (1991), and Gonzalez, J. & Tsien, R. Y. Biophy. J. 69:1272–1280 (1995)).

PFPs of the present invention can be immobilized in a host matrix, such as a polyacrylamide (PA) gel. Other possible hosts for PFPs include agarose gels, hydrogen-bonded polymers such as poly(vinyl alcohol), poly (electrolytes), viscous liquids, cell cytoplasm. The PA gel provides pore sizes small enough for immobilization of individual protein molecules (see, e.g., Fawcett, J. S. & Morris, C. J. O. R. Sep. Sci. 1:9 (1966)).

Immobilized PFPs can be imaged as single molecules (see, e.g., Dickson, R. M. et al. Science 274:966–969 (1996); and Moerner, W. E. Science, 265:46–53 (1994). PFPs can be used in biological applications such as marking cell structures with a focused beam and monitoring their subsequent diffusion or trafficking. For a description of marking cell structures with fluorescent proteins, see, e.g., Yokoe, H. & Meyer, T. Nature Biotechnology 14:1252 (1996).

Screening methods can be used to identify PFPs having an increased or particular photochromic response (see, e.g., U.S. Pat. No. 6,046,925). For example, host cells, e.g., bacteria can be transformed with PFP cDNA (containing a large number of different mutations) and spread onto agar plates following standard molecular biological methods such as described in Molecular Cloning, a Laboratory Manual, 2nd ed., by Sambrook, J., Fritsch, E. F. & Maniatis, T., Cold Spring Harbor Laboratory Press (1989). The plates can then be illuminated with two different wavelengths A and B in succession. Two separate images can be captured (I(A1) and I(B1)) with an electronic camera and computer system. The plate can then be illuminated with a high dose of light at a third wavelength C, which can be the same as A or B, or different from both. The third wavelength may photoisomerize any appropriately photochromic PFPs, resulting in a change in the fluorescence response of the plate. After the exposure, the plate is illuminated with the two original wavelengths A and B and two more images I(A2) and I(B2) are captured. The ratio images I(A2)/I(A1), I(B2)/I(B1), as well as the ratio of these two ratios, I(A2)I(B1)/I(A1) I(B2) can be calculated and displayed. Colonies can be identified that deviate significantly from the mean behavior by examination of the ratio images for any of these three ratios and the colonies of interest can be picked. Alternatively, the computer can robotically pick up colonies of interest using feature detection and mechanical manipulation capabilities. The method can be extended by skipping image capture step to obtain I(A1) and I(B1) using methods known in the art, see, e.g., U.S. Pat. No. 6,046,925.

Preferably, in the above procedures, an exact replica of the colonies on a plate is made. This can be done by pressing a nitrocellulose filter onto the agar plate so that some but not all the bacteria that make up each colony stick to the nitrocellulose. The nitrocellulose replica carries a spatially mirror-image replica of the colonies on the original agar plate. The light exposures and imaging can be performed on the replica on nitrocellulose because nitrocellulose has a lower background fluorescence than agar. However, the actual bacteria to be propagated can be picked off the corresponding colonies in the agar original, which has not been subjected to the potentially harsh treatments that might jeopardize the survival and subsequent multiplication of the bacteria. The computer system can reverse the mirror-image views of the replica colonies to ease registration of those images with the original agar plate.

Similar screenings can be performed with chemical treatments rather than light exposures. For example, the chemical treatments can include changing the pH, changing calcium ion concentration, adding cyclic GMP, adding a protein kinase, or adding a protease. The bacteria can be lysed so that added reagents can access PFPs expressed therein.

Accordingly, the invention comprises PFPs, PFP mutants, genetic sequences coding for such PFP amino acid sequences, expression vehicles containing the PFP genetic sequences, hosts transformed with such genetic sequences, recombinant PFPs, and PFP antisense RNAs produced by such transformed hosts. The invention further comprises antibodies directed against PFPs and/or fragments thereof or against PFP mutants.

The process for genetically engineering such protein sequences, according to the invention, is facilitated through the cloning of genetic sequences which are capable of encoding the peptide and through the expression of such genetic sequences. As used herein, the term "genetic sequences" is intended to refer to a nucleic acid molecule (preferably DNA). Genetic sequences which are capable of encoding proteins derived from a variety of sources. These sources include genomic DNA, cDNA, synthetic DNA, and combinations thereof. The preferred source of the genomic DNA or mRNA is *Physalia*. In a preferred embodiment, the source is *Physalia utriculus*. In another preferred embodiment, the source is tissue from the tentacle of *Physalia* . The mRNA may then be used to obtain cDNA by techniques known to those skilled in the art. Probes may be synthesized based on the nucleotide sequence of a PFP by methods known in the art.

PFP or fragment genomic DNA of the invention may or may not include naturally occurring introns. Moreover, such genomic DNA may be obtained in association with the 5' promoter region of a PFP gene sequences and/or with the 3' transcriptional termination region. Further, such genomic DNA may be obtained in association with the genetic sequences which encode the 5' non-translated region of a PFP mRNA and/or with the genetic sequences which encode the 3' non-translated region. To the extent that a host cell can recognize the transcriptional and/or translational regulatory signals associated with the expression of the mRNA and protein, the 5' and/or 3' non-transcribed regions of the native gene, and/or the 5' and/or 3' non-translated regions of the mRNA, may be retained and employed for transcriptional and translational regulation. PFP genomic DNA can be extracted and purified from a sample, e.g., a cell, tissue, or organism, by means well known in the art (for example, see Berger, S. L., et al., Eds., Guide to Molecular Cloning Techniques, Academic Press (1987)).

Alternatively mRNA can be isolated from any cell which produces or expresses a PFP, and used to produce cDNA by means well known in the art (for example, see Berger, S. L., et al., Eds., Guide to Molecular Cloning Techniques, Academic Press (1987)). Preferably, the mRNA preparation used will be enriched in mRNA coding for such protein, either naturally, by isolation from cells which are producing large amounts of the protein, or in vitro, by techniques commonly used to enrich mRNA preparations of specific sequences, including for example sucrose gradient centrifugation, or PCR. cDNA can then be prepared for example, by reverse transcription. The cDNA can then be amplified by PCR using suitable primers.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library. A DNA sequence encoding a PFP or its functional equivalents may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, J., et al., Molecular Cloning: A Laboratory Manual, 2d Ed., Cold Spring Harbor Laboratory Press, Planview, N.Y. (1989), and are well known in the art.

Libraries containing PFP clones may be screened and a PFP clone identified by any means which specifically selects for DNA encoding PFP such as, for example, (a) by hybridization with an appropriate nucleic acid probe(s) containing a sequence specific for the DNA of this protein, or (b) by hybridization-selected translational analysis in which native mRNA which hybridizes to the clone in question is translated in vitro and the translation products are further characterized, or, (c) if the cloned genetic sequences are themselves capable of expressing mRNA, by immunoprecipitation of a translated PFP or fragment product produced by the host containing the clone.

Oligonucleotide probes specific for a PFP which can be used to identify clones to this protein can be designed from knowledge of the amino acid sequence of a PFP. The sequence of amino acid residues in a peptide is designated herein either through the use of their commonly employed three-letter designations or by their single-letter designations. A listing of these three-letter and one-letter designations may be tound in textbooks such as Biochemistry, 2ed., Lehninger, A., Worth Publishers, New York, N.Y. (1975). When the amino acid sequence is listed horizontally, the amino terminus is intended to be on the left end whereas the caiboxy terminus is intended to be at the right end. T he residues of amino acids in a peptide may be separated by hyphens. Such hyphens are intended solely to facilitate the presentation of a sequence.

Because the genetic code is degenerate, more than one codon may be used to encode a particular amino acid (Watson, J. D., In: Molecular Biology of the Gene, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: Molecular Biology of the Gene, 3rd Ed., W. A. Benjamin, Inc., Menlo Park, Calif. (1977)), one or more different oligonucleotides can be identified from the amino acid sequence, each of which would he capable of encoding the present PFP or fragment protein. The probability that a particular oligonucleotide will, in fact, constitute the actual protein coding sequence can be estimated by considering abnormal base pairing relationships and the frequency with which a particular codon is actually used (to encode a particular amino acid) in eukaryotic cells. Such "codon usage rules" are disclosed by Lathe, et al., J. Molec. Biol. 183:1–12 (1985). Using the "codon usage rules" of Lathe, a single oligonucleotide sequence, or a set of oligonucleotide sequences, that contains a theoretical "most probable" nucleotide sequence capable of encoding a PFP sequence is identified.

The suitable oligonucleotide, or set of oligonucleotides, which is capable of encoding a fragment of a PFP gene (or which is complementary to such an oligonucleotide, or set of oligonucleotides) may be synthesized by means well known in the art (see, for example, S. A. Narang, Ed., Synthesis and Application of DNA and RNA, Academic Press, San Diego, Calif.) and employed as a probe to identify and isolate the cloned PFP gene by techniques known in the art. Techniques of nucleic acid hybridization and clone identification are disclosed by Maniatis, et al., Eds., Molecular Cloning, A Laboratory Manual, Cold Spring Harbor Laboratories, Cold Spring Harbor, N.Y., (1982); Berger, et al., Eds., Guide to Molecular Cloning Techniques, Academic Press, San Diego, Calif., (1988); Sambrook, J., et al., Molecular Cloning: A Laboratory Manual, 2d Ed., Cold Spring Harbor Laboratory Press, Planview, N.Y. (1989); and by Hames, et al., Eds., Nucleic Acid Hybridization, A Practical Approach, IRL Press, Washington, D.C., (1985), which references are herein incorporated by reference. Those members of the above-described gene library which are found to be capable of such hybridization are then analyzed to determine the extent and nature of the PFP encoding sequences which they contain.

To facilitate the detection of a desired PFP or fragment protein DNA encoding sequence, the above-described DNA probe is labeled with a detectable group or label. Such detectable group or label can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$ or the like. Any radioactive label may be employed which provides for an adequate signal and has a sufficient half-life. The oligonucleotide may be radioactively labeled, for example, by "nick-translation" by well-known means, as described in, for example, Rigby, et al., J. Mol Biol. 113:237 (1977) and by T4 DNA polymerase replacement synthesis as described in, for example, Deen, et al., Anal. Biochem. 135:456 (1983).

Alternatively, polynucleotides are also useful as nucleic acid hybridization probes when labeled with a non-radioactive marker such as biotin, an enzyme or a fluorescent or chemiluminescent group. See, for example, Leary, et al., Proc. Natl. Acad. Sci, USA 80:4045 (1983); Renz, et al., Nucl. Acids Res. 12:3435 (1984); and Renz, M., EMBO J. 6:817 (1983).

Thus, the actual identification of PFP encoding sequences permits the identification of a theoretical "most probable" DNA sequence, or a set of such sequences, capable of encoding such peptides. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a PFP gene.

In an alternative way of cloning a PFP gene, a library is prepared using an expression vector, by cloning DNA or, more preferably, cDNA prepared from a cell capable of expressing a PFP, into an expression vector. The library is then screened for members which express PFPs, for example, by screening, the library with antibodies directed to PFPs.

The above discussed methods are, therefore, capable of identifying genetic sequences which are capable of encoding PFPs or fragments thereof. In order to further characterize such genetic sequences, and, in order to produce the recombinant protein, it is desirable to express the proteins which these sequences encode. Such expression identities those clones which express proteins possessing characteristics of PFPs. Such characteristics may include the ability to specifically bind antibody to a PFP and the ability to elicit the production of an antibody or antibodies which are capable of binding to a PFP.

To express a PFP or a functional equivalent, or mutant thereof, transcriptional and translational signals recognizable by an appropriate host are necessary. Cloned PFP encoding sequences, obtained, for example, through the methods described above, and preferably in a double-stranded form, may be operably linked to sequences controlling transcriptional expression in an expression vector, and introduced into a host cell, either prokaryotic or eukaryotic, to produce recombinant PFP or a functional equivalent thereof. Depending upon which strand of a PFP encoding sequence is operably linked to the sequences controlling transcriptional expression, it is also possible to express PFP antisense RNA or a functional equivalent thereof.

Expression of a PFP in different hosts may result in different post-translational modifications which may alter the properties of a PFP. The present invention encompasses the expression of a PFP, or functional equivalent thereof, or PFP mutant, in prokaryotic or eukaryotic cells, and particularly, eukaryotic expression is preferred.

Preferred prokaryotic hosts include bacteria such as *E. coli, Bacillus, Streptomyces, Pseudomonas, Salmonella, Serratia*, etc. The most preferred prokaryotic host is *E. coli*. Other enterobacteria such as *Salmonella typhimurium* or *Serratia marcescens*, and various *Pseudomonas* species may also he utilized. Under such conditions, the protein may not be glycosylated. The prokaryotic host must be compatible with the replicon and control sequences in the expression plasmid.

To express a PFP (or a functional equivalent thereof) or PFP mutant in a prokaryotic cell (such as, for example, *E. coli, B. subtilis, Pseudomonas, Streptomices*, etc.), the PFP encoding sequence is operably linked to a functional prokaryotic promoter. Such promoters may be either constitutive or, more preferably, regulatable (i.e., inducible or derepressible). Examples of constitutive promoters include the int promoter of bacteriophage lambda, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of *E. coli*, the α-amylase (Ulmanen, I., et al., J. Bacteriol. 162:176–182 (1985)) and the sigma-28-specific promoters of *B. subtilis* (Gilman, M. Z., et al., Gene 32:11–20 (1984)), the promoters of the bacteriophages of *Bacillus* (Gryczan, T. J., The Molecular Bioloty of the *Bacilli*, Academic Press, Inc., N.Y. (1982)), and *Streptomyces* promoters (Ward, J. M., et al., Mol. Gen. Genet. 203:468–478 (1986)). Prokaryotic promoters are reviewed by Glick, B. R., (J. Ind. Microbial. 1:277–282 (1987)); Cenatiempo, Y. (Biochimie 68.505–516 (1986)); and Gottesman, S. (Ann. Rev. Genet. 18:415–442 (1984)).

Proper expression in a prokaryotic cell also requires the presence of a ribosome binding site upstream of the gene-encoding sequence. Such ribosome binding sites are disclosed, for example, by Gold, L., et al. (Ann. Rev. Microbial. 35:365–404 (1981)).

Especially preferred eukaryotic hosts include mammalian cells either in vivo, in animals or in tissue culture. General principles of mammalian cell culture are known in the art and are described, for example, in Butler, M. and Dawson, M., Eds., Cell Culture LabFax, Bios Scientific Publishers Ltd., Oxford, UK and Academic Press, Inc., San Diego, Calif., Publishers (1992), and references cited therein.

Expression of a PFP in eukaryotic hosts requires the use of regulatory regions functional in such hosts, and preferably eukaryotic regulatory systems. A wide variety of transcriptional and translational regulatory sequences can be employed, depending upon the nature of the eukaryotic host.

The transcriptional and translational regulatory signals can also be derived from the genomic sequences of viruses which intect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, et al., J. Mol. Appl. Gen. 1:273–288 (1982)); the TK promoter of Herpes virus (McKnight, S., Cell 31:355–365 (1982)); the SV40 early promoter (Benoist, et al., Nature (London) 290:304–310 (1981)); and the HCMV promoter (Boshart, et al., Cell 41:521 (1985)); in yeast, the yeast gal4 gene promoter (Johnston, et al., Proc. Natl. Acad. Sci. USA 79:6971–6975 (1982); Silver, et al., Proc. Natl. Acad. Sci. USA 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes a PFP, or a functional equivalent thereof does not contain any intervening codons which are capable of encoding a methionine. The presence of such codons results either in the formation of a fusion protein (if the AUG codon is in the same reading frame as a PFP encoding DNA sequence) or a frame-shift mutation (if the AUG codon is not in the same reading frame as aPFP encoding sequence).

The sequence encoding a PFP or fragment thereof may be linked to a signal sequence which will allow secretion of the protein from or the compartmentalization of the protein in, a particular host. Such signal sequences may be designed with or without specific protease sites such that the signal peptide sequence is amenable to subsequent removal.

Transcriptional initiation regulatory signals can be selected which allow for repression or activation, so that expression of the operably linked genes can he modulated. Of interest are regulatory signals which are temperature-sensitive, such that by varying the temperature, expression can be repressed or initiated, or which are subject to chemical regulation, e.g., by a metabolite. Also of interest are constructs wherein a PFP mRNA and antisense RNA are provided in a transcribable form, but with different promoters or other transcriptional regulatory elements such that induction of PFP mRNA expression is accompanied by repression of antisense RNA expression, and/or repression of PFP mRNA expression is accompanied by induction of antisense RNA expression. To express PFP antisense RNA sequences a tranlation signal is not necessary.

If desired, the non-transcribed and/or non-translated regions 3' to the sequence coding for a PFP can be obtained by the above-described cloning methods. The 3'-non-transcribed region may be retained for its transcriptional termination regulatory sequence elements; the 3'-nontranslated region may be retained for its translation termination regulatory sequence elements, or for those elements which direct polyadenylation in eukaryotic cells. Where the native expression control sequence signals do not function satisfactorily in the host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the a PFP DNA construct into the host cell chromosomal DNA, or to allow it to exist in an extrachromosomal form.

If a PFP DNA encoding sequence and an operably linked promoter are introduced into a recipient eukaryotic cell as a non-replicating DNA (or RNA) molecule, which may either be a linear molecule or a closed covalent circular molecule which is incapable of autonomous replication, then the expression of a PFP may occur through the transient expression of the introduced sequence.

Genetically stable transformants may be constructed with vector systems, or transformation systems, whereby bak DNA is integrated into the host chromosome. Such integration may occur de novo within the cell or, in a preferred embodiment, be assisted by transformation with a vector which functionally inserts itself into the host chromosome, for example, with retroviral vectors, transposons or other DNA elements which promote integration of DNA sequences into chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the case with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, et al., Miami Wntr. Symp. 19:265–274 (1982); Broach, J. R., The Molecular Biology of the Yeast Saccharomyces: Life Cycle and Inheritance, Cold Spring Harbor Laboratory, Cold Spring Harbor, N.Y., pp. 445–470 (1981); Broach, J. R., Cell 28:203–204 (1982); Bollon, et sl., J. Clin, Hematol. Oncol. 10:39–48 (1980); Maniatis, T., "Gene Expression," In: Cell Biology: A Comprehensive Treatise, Vol. 3, Academic Press, New York, pp. 563–608 (1980)), and are commercially available. For example, mammalian expression vector systems which utilize the MSV-LTR promoter to drive expression of the cloned gene, and in which it is possible to contransfect with a helper virus to amplify plasmid copy number, and integrate the plasmid into the chromosomes of host cells, have been described (Perkins, et (al., Mol. Cell Biol. 3:1123 (1983); Clontech, Palo Alto, Calif.).

Once the vector or DNA sequence containing the construct(s) is prepared for expression, the DNA construct (s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of a PFP, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein can be isolated and purified in accordance with conventional conditions, such as extraction, precipitation, chromatography, affinity chromatography, electrophoresis, or the like. Alternatively, a PFP can be used without purification or with partial purification.

PFPs can be purified by growing the transformed host cells under suitable conditions which are well known in the art, the cells can be harvested and disrupted to extract total cellular protein. The protein can then, for example, be placed on a sizing column such as sepharose or agarose beads, and proteins of the correct molecular weight can be collected.

Further purification can be effected by use of an anti-PFP antibody. Such an antibody can be used to immunoprecipitate PFPs from the set of cellular proteins of the correct approximate molecular weight. Such antibodies can, for example, be raised against polypeptides synthesized according to the sequence or subsequences of a known PFP sequence. Alternatively, the antibodies can be raised against fusion proteins, which contain PFP sequences as well as those of other proteins. After immunoprecipitation, the PFP can be released from the antibodies to provide a substantially pure preparation of a PFP.

DNA sequences encoding a PFP of the present invention may be used to obtain PFP antisense RNA genetic sequences, in as much as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of a PFP antisense RNA in the transformed cell. Antisense RNA and its expression may be used to interact with an endogenous PFP DNA or RNA in a manner which inhibits or represses transcription or translation of PFP genes in a highly specific manner. Use of antisense RNA probes to block gene expression is described, for example, in Lichtenstein, C., Nature 333:801–802 (1988).

As used herein, the term "PFP" or "*Physalia* fluorescent protein" refers to a protein having the characteristics of a PFP described herein, and to peptides and/or molecules capable of mimicking the structure and/or function and/or activity of a PFP, and functional equivalents thereof.

By "functional equivalent" is meant a peptide possessing a biological activity or immunological characteristic substantially similar to that of a PFP, and is intended to include "fragments", "variants", "analogs", "homologs", "derivatives", "chemical derivatives" or "synthetic derivative" possessing such activity or characteristics. Thus, the present invention encompasses functional equivalents of PFPs that may not share an identical amino acid sequence, and conservative or non-conservative amino acid substitutions of conventional or unconventional amino acids.

The isolated PFPs of the present invention, preferably recombinant PFPs, and more preferably a PFP fusion polypeptides can be used in a variety of methods and compositions that exploit the autofluorescent properties of the PFPs. These methods include, but are not limited to, the use of a PFP as a reporter molecule in cell screening assays, including intracellular assays; the use of a PFP as a scaffold protein for fusions with random peptide libraries. Similarly, compositions of PFPs are provided, including constructs of PFPs, such as fusion polypeptides, that include PFPs as reporter genes, retroviral constructs including PFPs and internal ribosome entry sites (IRES), etc. Basically, the invention provides a number of novel uses for the PFPs of the present invention, similar to those described for Green Fluorescent Protein (GFP) in WO 95/07463, hereby incorporated by reference in its entirety.

Described more fully below are recombinant PFPs, e.g., PFP fusion polypeptides, and novel uses for such PFPs.

In a preferred embodiment, a nucleic acid encoding a PFP, or amino acid encoding a PFP, is identified by substantial homology to a nucleic acid or amino acid sequence, respectively, encoding a known PFP. In a preferred embodiment, a known PFP is a protein having a property of a PFP as described herein, e.g., an excitation wavelength in a range of about 210–550 nm, or an emission wavelength in a range of about 400–95 nm: Such homology can be based upon the overall nucleic acid or amino acid sequence. In a preferred embodiment, a protein is identified as a PFP if the overall homology of the amino acid sequence encoding the PFP about 75%, more preferably greater than about 80%, even more preferably greater than about 85% and most preferably greater than 90% homologous to the amino acid sequence encoding a known PFP. In another preferred embodiment the amino acid sequence encoding the protein is about 93 to 95 or 98% homologous to the amino acid sequence encoding a known PFP and, thus, is the protein is identified as a PFP of the present invention.

Homology in this context means sequence similarity or identity, with identity being preferred. This homology can be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc Natl. Acad. Sci. U.S.A. 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), or the Best Fit sequence program described by Devereux et al., Nucl. Acid Res. 12:387–95 (1984), preferably using the default settings, or by inspection.

In a preferred embodiment, similarity is calculated by FastDB based upon the following parameters: mismatch penalty of 1.0; gap size penalty of 0.33, joining penalty of 30.0 ("Current methods in Comparison and Analysis", Macromolecule Sequencing and Synthesis, selected methods and Applications, pp. 127–149 (1998), Alan R. Liss, Inc.).

Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, J. Mol. Evol. 35:351–60 (1987); the method is similar to that described by Higgins and Sharp CABIOS 5:151–3 (1989). Useful PILEUP parameters including a default gap weight of 3.00, a default gap length weight of 0.10, and weighted end gaps.

An additional example of a useful algorithm is the BLAST algorithm, described in Altschul et al., J. Mol. Biol. 215: 403–410 (1990) and Karlin et al., Proc. Natl. Acad. Sci. U.S.A. 90:5873–87 (1993). A particularly useful BLAST program is the WU-BLAST-2 program which was obtained from Altschul et al., Methods in Enzymology 266:460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of PFPs. A preferred method utilizes the BLASTN module of WU-BLAST-2 set to the default parameters, with overlap span and overlap fraction set to 1 and 0.125, respectively.

An additional useful algorithm is gapped BLAST as reported by Altschul et al., Nucl. Acid Res. 25:3389–3402 (1997). Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

The alignment may include the introduction of gaps in the sequences to be aligned. In addition, for sequences which contain either more or fewer amino acids than the protein sequences of a known PFP it is understood that the percentage of homology will be determined based on the number of homologous amino acids in relation to the total number of amino acids. Thus, the PFPs of the present invention may be shorter or longer than the amino acid sequences of a known PFP, e.g., a wild-type PFP or recombinant PFP. Thus, in a preferred embodiment, included within the definition of PFPs are portions or fragments of the sequences of a known PFP. Portions or fragments of PFPs are considered PFPs of the present invention if a) they share at least one antigenic epitope; or b) have at least the indicated homology; c) preferably have PFP biological activity, e.g., including, but not limited to, autofluorescence; or d) fold into a stable structure that is similar to a known PFP, e.g, a wild-type PFP or recombinant PFP.

For example, PFP deletion mutants can be made using methods known in the art. See e.g., Phillips et al., Current Opin. Structural Biol. 7:821 (1997)). In a preferred embodiment, the PFPs are derivative or variant PFPs. That is, as described more fully below, the derivative PFP will contain at least one amino acid substitution, deletion or insertion, with amino acid substitutions being particularly preferred. The amino acid substitution, insertion or deletion may occur at any residue within the PFP. These variants ordinarily are prepared by site specific mutagenesis of nucleotides in the DNA encoding a PFP, using cassette or PCR mutagenesis or other techniques well known in the art, to produce DNA encoding the variant, and thereafter expressing the DNA in recombinant cell culture as is known in the art and described herein. However, variant PFP fragments having up to about 100–150 residues may be prepared by in vitro synthesis using established techniques.

Amino acid sequence variants are characterized by the predetermined nature of the variation, a feature that sets them apart from naturally occurring allelic or interspecies variation of a PFP amino acid sequence. The variants typically exhibit the same qualitative biological activity as the naturally occurring analogue, although variants can also be selected which have modified characteristics as will be more fully described below. That is, in a preferred embodiment, when a non-wild-type PFP is used, the derivative preferably has at least 1% of wild-type fluorescence, with at least about 10% being preferred, at least about 50–60% being particularly preferred and 95% to 98% to 100% being especially preferred. In general, what is important is that there is enough fluorescence to allow sorting and/or detection above background, for example using a fluorescence-activated cell sorter (FACS) machine. However, in some embodiments, for example when PFP fusion polypeptides are made, it is possible to detect the fusion proteins non-fluorescently, using, for example, antibodies directed to either an epitope tag (i.e. purification sequence) or to a PFP itself. In this case a PFP scaffold does not have to be fluorescent, if it can be shown that the PFP is folding correctly and/or reproducibly.

Thus, a PFP of the present invention may be a wild-type or a variant thereof. PFP variants may be one or more of three classes: substitutional, insertional or deletional variants. These variants ordinarily are prepared by site specific mutagenesis of nucleotides in the DNA encoding a PFP, using cassette or PCR mutagenesis or other techniques well known in the art, to produce a DNA encoding a PFP variant, and thereafter expressing the DNA in recombinant cell culture as described herein. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of PFP amino acid sequences. The variants typically exhibit the same qualitative biological activity as the naturally occurring analogue, although variants can also be selected which have modified characteristics as will be more fully described below.

While the site or region for introducing an amino acid sequence variation is predetermined, the mutation per se need not be predetermined. For example, in order to optimize the performance of a mutation at a given site, random mutagenesis may be conducted at the target codon or region and the expressed scaffold variants screened for the optimal combination of desired activity. Techniques for making substitution mutations at predetermined sites in DNA having a known sequence are well known, for example, M13 primer mutagenesis and PCR mutagenesis. Screening of the mutants is done using assays of scaffold protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of a PFP are desired, substitutions are generally made in accordance with Table 1 below.

TABLE I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having-a bulky side chain, e.g. phenylalanine, is substituted for (or by) one not having a side chain, e.g. glycine.

As described above, the variants typically exhibit the same qualitative biological activity (i.e. fluorescence) although variants also are selected to modify the characteristics of a PFP as needed.

In a preferred embodiment specific residues of a PFP are substituted, resulting in proteins with modified characteristics. Such substitutions may occur at one or more residues, with 1–10 substitutions being preferred. Preferred characteristics to be modified include range of spectral emission, including shifts in peak emission, rate of folding, stability, expression levels, toxicity, and emission intensity.

In addition, PFPs can be made that are longer than the wild-type, for example, by the addition of epitope or purification tags, the addition of other fusion sequences, as is more fully described below.

In a preferred embodiment, a PFP is fused to a protein of interest. This may be done, for example, to allowing tracking or localization of the protein of interest to a particular subcellular location, or to allow for quantification of expression.

In a preferred embodiment, a PFP is fused to a random peptide to form a fusion polypeptide. With reference to protein, "fused" or "operably linked" herein is meant that the random peptide, as defined below, and a PFP are linked together, in such a manner as to minimize the disruption to the stability of the PFP structure (i.e., it can retain biological activity). That is, a PFP preferably retains its ability to fluoresce, or maintains a Tm of at least 42 C. As described below, a PFP fusion polypeptide (or fusion polynucleotide encoding the fusion polypeptide can comprise further components as well, including multiple peptides at multiple loops, fusion partners, etc.

A PFP fusion polypeptide preferably includes additional components, including, but not limited to, fusion partners and linkers.

In a preferred embodiment, the random peptide is fused to the N-terminus of a PFP. The fusion can be direct, i.e. with no additional residues between the C-terminus of the peptide and the N-terminus of a PFP, or indirect; that is, intervening amino acids are used, such as one or more fusion partners, including a linker. In this embodiment, preferably a presentation structure is used, to confer some conformational stability to the peptide. Particularly preferred embodiments include the use of dimerization sequences.

In one embodiment, N-terminal residues of a PFP are deleted, i.e. one or more amino acids of a PFP can be deleted and replaced with the peptide. However, as noted above, deletions of more than 7 amino acids may render a PFP less fluorescent, and thus larger deletions are generally not preferred. In a preferred embodiment, the fusion is directly to the first amino acid of a PFP.

In a preferred embodiment, the random peptide is fused to the C-terminus of a PFP. As above for N-terminal fusions, the fusion can be direct or indirect, and C-terminal residues may be deleted.

In a preferred embodiment, peptides and fusion partners are added to both the N- and the C-terminus of a PFP. In a preferred embodiment, the N- and C-terminus of a PFP are putatively on the same "face" of the protein, in spatial proximity, and form a non-covalently "circular" PFP using the components of the invention. Thus for example, the use of dimerization sequences can allow a noncovalently cyclized protein by attaching a first dimerization sequence to either the N- or C-terminus of a PFP, and adding a random peptide and a second dimerization sequence to the other terminus, a large compact structure can be formed.

In a preferred embodiment, a random peptide is fused to an internal position of a PFP, i.e., the peptide is inserted at an internal position of the PFP. While the peptide can be inserted at virtually any position, preferred positions include insertion at the very tips of protein "loops" on the surface of a protein, to minimize disruption of protein structure. Libraries of random peptides (or, alternatively single peptides) can be inserted into or replace external loops. As described below, this can be either an insertion (e.g. without replacing any residues), or the addition of the random peptides or other fusion partners results in the replacement of one or more of the native residues.

In a preferred embodiment, the random peptide is inserted, without any deletion of PFP residues. The insertion point can be between two amino acids in a PFP, adding the new amino acids of the peptide and fusion partners, including linkers. Generally, when linkers are used, the linkers are directly fused to the PFP, with additional fusion partners, if present, being fused to the linkers and the peptides.

In a preferred embodiment, the peptide is inserted into a PFP, with one or more PFP residues being deleted; that is, the random peptide (and fusion partners, including linkers) replaces one or more PFP residues. In general, when linkers are used, the linkers are attached directly to a PFP, thus it is linker residues which replace PFP residues. In general, when residues are replaced, from one to five residues of a PFP are deleted, with deletions of one, two, three, four and five amino acids all possible.

In a preferred embodiment, peptides (including fusion partners, if applicable) can be inserted into more than one loop of the scaffold at a time. Thus, for example, adding peptides to two loops can increase the complexity of the library but still allow presentation of these loops on the same face of the protein. Similarly, it is possible to add peptides to one or more loops and add other fusion partners to other loops, such as targeting sequences, etc.

Thus, the present invention provides fusion polypeptides comprising a PFP and random peptides. Similarly, the invention provides fusion nucleic acids encoding PFP fusion polypeptides. In addition, to facilitate the introduction of random peptides into a PFP, a preferred embodiment provides PFP nucleic acids with a multisite cloning site inserted into at least one loop described above.

In a preferred embodiment, the PFP fusion polypeptides further comprise fusion partners. By "fusion partner" herein is meant a sequence that is associated with the random peptide that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the peptides in a conformationally restricted or stable form; b) targeting sequences, defined below, which allow the localization of the peptide into a subcellular or extracellular compartment; c) rescue sequences as defined below, which allow the purification or isolation of either the peptides or the nucleic acids encoding them; d) stability sequences, which confer stability or protection from degradation to the peptide or the nucleic acid encoding it, for example resistance to proteolytic degradation; e) linker sequences, which conformationally decouple the random peptide elements from the scaffold itself, which keep the peptide from interfering with scaffold folding; or f), any combination of a), b), c), d) and e) as well as linker sequences as needed.

In a preferred embodiment, the fusion partner is a presentation structure. By "presentation structure" or grammatical equivalents herein is meant a sequence, which, when fused to peptides, causes the peptides to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmacophore models and pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as described below, in which elements of the presentation structure are included within the random peptide sequence. To increase the functional isolation of the randomized expression product, the presentation structures are selected or designed to have minimal biologically activity when expressed in the target cell.

Preferred presentation structures maximize accessibility to the peptide by presenting it on an exterior surface such as a loop, and also cause further conformational constraints in a peptide. Accordingly, suitable presentation structures include, but are not limited to, dimerization sequences, minibody structures, loops on β-turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows:
MGCAALESEVSALESEVASLESEVAALGRGDMP LAAVKSKLSAVKSKLASVKSKLAACGPP (SEQ. ID NO:1). The underlined regions represent a coiled-coil leucine zipper region defined previously (see Martin et al., EMBO J. 13(22):5303–5309 (1994), incorporated by reference). The bolded GRGDMP region represents the loop structure and when appropriately replaced with randomized peptides (i.e. peptides, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference)

Investigators have shown this minimal domain is stable in solution and have used phage selection systems in combinatorial libraries to select minibodies with peptide regions exhibiting high affinity, Kd=10–7, for the pro-inflammatory cytokine IL-6.

A preferred minibody presentation structure is as follows:
MGRNSQATSGFTFSHFYMEWVRGGEYIAASR HKHNKYTTEYSASVKGRYIVSRDTSQSILYLQ KKKGPP (SEQ. ID NO:2). The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred ex vivo, for example when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the presentation sequence confers the ability to bind metal ions to confer secondary structure. Thus, for example, $C_2H_2$ zinc finger sequences are used; C2H2 sequences have two cysteines and two histidines placed such that a zinc ion is chelated. Zinc finger domains are known to occur independently in multiple zinc-finger peptides to form structurally independent, flexibly linked domains. See J. Mol. Biol. 228:619 (1992). A general consensus sequence is (5 amino acids)-C-(2 to 3 amino acids)-C-(4 to 12 amino acids)-H-(3 amino acids)-H-(5 amino acids) (SEQ. ID NO:3). A preferred example would be -FQCEEC-random peptide of 3 to amino acids-HIRSHTG- (SEQ. ID NO:4).

Similarly, CCHC boxes can be used (see Biochem. Biophys. Res. Commun. 242:385 (1998)), that have a consensus seqeunce -C-(2 amino acids)-C-(4 to 20 random peptide)-H-(4 amino acids)-C- (SEQ. ID NO:5) (see Bavoso et al., Biochem. Biophys. Res. Comm. 242(2):385 (1998), hereby incorporated by reference. Preferred examples include (1) -VKCFNC-4 to 20 random amino acids-HTARNCR- (SEQ. ID NO:1), based on the nucleocapsid protein P2; (2) a sequence modified from that of the naturally occuring zinc-binding peptide of the Lasp-1 LIM domain (Hammarstrom et al., Biochem. 35:12723 (1996)); and (3) -MNPNCARCG4 to 20 random amino acids-HKACF- (SEQ. ID NO:7), based on the nmr structural ensemble 1ZFP (Hammarstrom et al., Biochem. 35 U.S.C. 35(39):12723 (1996).

In a preferred embodiment, the presentation structure is a dimerization sequence, including self-binding peptides. A dimerization sequence allows the non-covalent association of two peptide sequences, which can be the same or different, with sufficient affinity to remain associated under normal physiological conditions. These sequences may be used in several ways. In a preferred embodiment, one terminus of the random peptide is joined to a first dimerization sequence and the other terminus is joined to a second dimerization sequence, which can be the same or different from the first sequence. This allows the formation of a loop upon association of the dimerizing sequences. Alternatively, the use of these sequences effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two different sequences that associate. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure. The use of dimerization sequences allows the "circularization" of the random peptides; that is, if a dimerization sequence is used at each terminus of the peptide, the resulting structure can form a "stem-loop" type of structure. Furthermore, the use of dimerizing sequences fused to both the N- and C-terminus of a PFP can form a noncovalently cyclized scaffold random peptide library.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods. See, e.g., U.S. Ser. No. 60/080,444, filed Apr. 2, 1998, hereby incorporated by reference in its entirety. Particularly preferred dimerization peptide sequences include, but are not limited to, -EFLIVKS-, -EEFLIVKKS-, -FESIKLV-, and -VSIKFEL- (SEQ. ID NO:8–11).

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the peptides to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val (SEQ. ID NO:12)), Kalderon (1984), et al., Cell, 39:499–509; the human retinoic acid receptor-β nuclear localization signal (ARRRRP (SEQ. ID NO:13)); NFkB p50 (EEVQRKRQKL (SEQ. ID NO:14); Ghosh et al., Cell 62:1019 (1990); NFkB p65 (EEKRKRTYE (SEQ. ID NO:15); Nolan et al., Cell 64:961 (1991); and others (see for example Boulikas, J. Cell. Biochem. 55(1):32–58 (1994), hereby incorporated by reference) and double basic NLSs exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp (SEQ. ID NO:16)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized epression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product□containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. The TM and ssTM are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains. Preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al., Eur. J. Biochem. 174:671 (1988)) and insulin receptor β-chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8
(MASPLTRFLSLNLLLLGESILGSGEAKPQAP (SEQ. ID NO:17); Nakauchi et al., PNAS USA 82:5126 (1985) and 1–21 in the case of ICAM-2 (MSSFGYRTLTVALFTLICCPG (SEQ. ID NO:18); Staunton et al., Nature (London) 339:61 (1989)). These leader sequences deliver the construct to the membrane while the hydrophobic transmembrane domains, placed 3' of the random peptide region, serve to anchor the construct in the membrane. These transmembrane domains are encompassed by amino acids 145–195 from CD8 (PQRPEDCRPRGSVKGTGLDFACDIYI-WAPLAGICVALLLSLIITLICYHSR (SEQ. ID NO:19); Nakauchi, supra) and 224–256 from ICAM-2 (MVIIVTVVSVLLSLFVTSVLLCFIFGQHLRQQR (SEQ. ID NO:20); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ. ID NO:21), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ. ID NO:22)(see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSD-SEEELPTRL (SEQ. ID NO:23), with the bold cysteines being palmitolyated; Stoffel et al., J. Biol. Chem 269:27791 (1994)); from rhodopsin (KQFRNCMLTSLCCGKNPLGD (SEQ. ID NO:24); Barnstable et al., J. Mol. Neurosci. 5(3):207 (1994)); and the p21 H-ras 1 protein (LNPPDESGPGCMSCKCVLS (SEQ. ID NO:25); Capon et al., Nature 302:33 (1983)).

In a preferred embodiment, the targeting sequence is a lysozomal targeting sequence, including, for example, a lysosomal degradation sequence such as Lamp-2 (KFERQ (SEQ. ID NO:26); Dice, Ann. N.Y. Acad. Sci. 674:58 (1992); or lysosomal membrane sequences from Lamp-1 (MLIPIAGFFALAGLVLIVLIAYL*IGRKRSHAGYQTI* (SEQ. ID NO:27), Uthayakumar et al., Cell. Mol. Biol. Res. 41:405 (1995)) or Lamp-2 (LVPIAVGAALAGVLILVL-LAYFIG*LKHHHAGYEQF* (SEQ. ID NO:28), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ. ID NO:29); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ. ID NO:30); Schatz, supra); mitochondrial intermembrane space sequences (yeast cytochrome c1; MFSMLSKRWAQRTL-SKSFYSTATGAASKSGKLTQ KLVTAGVAAAGI-TASTLLYADSLTAEAMT A (SEQ. ID NO:31); Schatz, supra) or mitochondrial outer membrane sequences (yeast 70 kD outer membrane protein; MKSFITRNKTAIL-ATVAATGTAIGAYYYYNQLQQQQQRGKK (SEQ. ID NO:32); Schatz, supra).

The target sequences may also be endoplasmic reticulum sequences, including the sequences from calreticulin (KDEL (SEQ. ID NO:33); Pelham, Royal Society London Transactions B; 1–10 (1992)) or adenovirus E3/19K protein (LYLSRRSFIDEKKMP (SEQ. ID NO:34); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ. ID NO:25), with the bold cysteine farnesylated; Capon, supra); geranylgeranylation sequences (for example, protein rab-5A; LTEPTQPTRNQCCSN (SEQ. ID NO:35), with the bold cysteines geranylgeranylated; Farnsworth, PNAS USA 91:11963 (1994)); or destruction sequences (cyclin B1; RTALGDIGN (SEQ. ID NO:36); Klotzbucher et al., EMBO J. 1:3053 (1996)).

In a preferred embodiment, the targeting sequence is a secretory signal sequence capable of effecting the secretion of the fusion polypeptide. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ. ID NO:37); Villinger et al., J. Immunol. 155:3946 (1995)), growth hormone (MATGSRTSLLLAFGLLCLPWLQEG-SAFPT (SEQ. ID NO:38); Roskam et al., Nucleic Acids Res. 7:30 (1979)); preproinsulin (MALWMRLLPLLALLAL-WGPDPAAAFVN (SEQ. ID NO:39); Bell et al., Nature 284:26 (1980)); and influenza HA protein (MKAKLLVLLYAFVAGDQI (SEQ. ID NO:40); Sekiwawa et al., PNAS 80:3563)), with cleavage between the non-underlined-underlined junction. A particularly preferred secretory signal sequence is the signal leader sequence from the secreted cytokine IL4, which comprises the first 24 amino acids of IL-4 as follows:

MGLTSQLLPPLFFLLACAGNFVHG (SEQ. ID NO:41).

In a preferred embodiment, the fusion partner of a PFP is a rescue sequence. A rescue sequence is a sequence which may be used to purify or isolate either the peptide or the nucleic acid encoding it. Thus, for example, peptide rescue sequences include purification sequences such as the His6 tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, GST, and Strep tag I and II.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner of a PFP is a stability sequence to confer stability to the peptide or the nucleic acid encoding it. Thus, for example, peptides may be stabilized by the incorporation of glycines after the initiation methionine (MG or MGG 0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the peptide structure. Thus, preferred stability sequences are as follows: $MG(X)_n GGPP$, where X is any amino acid and n is an integer of at least four.

The fusion partners of PFPs may be placed N-terminal, C-terminal, internal of a PFP, as the biology and activity permits. In addition, while the discussion has been directed to the fusion of fusion partners to the peptide portion of a PFP fusion polypeptide, it is also possible to fuse one or more of these fusion partners to a PFP portion of the fusion polypeptide. Thus, for example, the PFP may contain a targeting sequence (either N-terminally, C-terminally, or internally, as described below) at one location, and a rescue sequence in the same place or a different place on the molecule. Thus, any combination of fusion partners and peptides and PFPs may be made.

In a preferred embodiment, the fusion partners of a PFP includes a linker or tethering sequence. Linker sequences between various targeting sequences (for example, membrane targeting sequences) and the other components of the constructs (such as the randomized peptides) may be desirable to allow the peptides to interact with potential targets unhindered. For example, useful linkers include glycine polymers $(G)_n$, glycine-serine polymers (including, for example, $(GS)_n$, $(GSGGS)_n$ (SEQ. ID NO:43) and $(GGGS)_n$ (SEQ. ID NO:44), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted tan residues with longer side chains (see Scheraga, Rev. Computational Chem. III73–142 (1992)). Secondly, serine is hydrophilic and therefore able to solubilize what could be a globular glycine chain. Third, similar chains have been shown to be effective in joining subunits of recombinant proteins such as single chain antibodies.

In a preferred embodiment, the peptide is connected to a PFP via linkers. That is, while one embodiment utilizes the direct linkage of the peptide to a PFP or of the peptide and any fusion partners to a PFP, a preferred embodiment utilizes linkers at one or both ends of the peptide. That is, when attached either to the N- or C-terminus, one linker may be used. When the peptide is inserted in an internal position, as is generally described below, preferred embodiments utilize at least one linker and preferably two, one at each terminus of the peptide. Linkers are generally preferred in order to conformationally decouple any insertion sequence (i.e. the peptide) from a PFP structure itself, to minimize local distortions in the PFP structure that can either destabilize folding intermediates or allow access to a PFP fluorophore, which could decrease (or eliminate) PFP fluorescence due to exposure to exogeneous collisional fluorescence quenchers (see, e.g., Phillips, Curr. Opin. Structural Biology 7:821 (1997), hereby incorporated by reference in its entireity).

Accordingly, as described below, when the peptides are inserted into internal positions in a PFP, preferred embodiments utilize linkers, and preferably (gly)n linkers, where n is 1 or more, with n being two, three, four, five and six, although linkers of 7–10 or more amino acids are also possible. Generally in this embodiment, no amino acids with β-carbons are used in the linkers.

In addition, the fusion partners of a PFP, including presentation structures, may be modified, randomized, and/or matured to alter the presentation orientation of the randomized expression product. For example, determinants at the base of a peptide loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences. As will be appreciated by those in the art, using a base vector that contains a cloning site for receiving random and/or biased libraries, one can cassette in various fusion partners 5' and 3' of the library. In addition, as discussed herein, it is possible to have more than one variable region in a construct, either to together form a new surface or to bring two other molecules together. Similarly, as more fully described below, it is possible to have peptides inserted at two or more different peptide loops of a PFP, preferably but not required to be on the same "face" of the PFP.

The invention further provides fusion nucleic acids encoding the PFP fusion polypeptides of the present invention. The fusion nucleic acids and expression of protein products from such nucleic acids can be prepared as described above concerning the construction and expression of recombinant PFPs. In general, recombinant methods known in the art can be used to construct fusion nucleic acids encoding a fusion polypeptide.

As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Specifically contemplated is each and every possible variation of a polynucleotide that could be made by selecting combinations based on the possible codon choices, and all such variations are to be considered specifically disclosed and equivalent to the sequences of a known PFP. Codons are preferably selected to fit the host cell in which the enzyme is being produced; that is, codon usage for yeast is used to express in yeast; codon usage for mammalian cells is used to express in mammalian cells; etc. Selection of codons to maximize expression of proteins in a heterologous host is a known technique.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

With reference to nucleic acid, a nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

The fusion nucleic acids are introduced into the cells for screening, as is more fully described below. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The candidate nucleic acids may stably integrate into the genome of the host cell (for example, with retroviral introduction, described below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

The PFP fusion polypeptides of the present invention are produced by culturing a host cell transformed with an expression vector containing nucleic acid encoding a fusion protein, under the appropriate conditions to induce or cause expression of the fusion protein, as described above. The conditions appropriate for fusion protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

In a preferred embodiment, the PFP fusion polypeptides are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA.

A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As described herein, a particularly preferred method utilizes retroviral infection, as described in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the fusion nucleic acid.

In a preferred embodiment, the PFP fusion polypeptides are expressed in bacterial systems. Bacterial expression systems are well known in the art.

In one embodiment, fusion proteins are produced in insect cells. Expression vectors for the transformation of insect cells, and in particular, baculovirus-based expression vectors, are well known in the art.

In a preferred embodiment, fusion protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.*

In addition, the PFP fusion polypeptides of the invention may be further fused to other proteins, if desired, for example to increase expression.

In one embodiment, the fusion nucleic acids, proteins and antibodies of the invention are labeled with a label other than the PFP. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the fusion nucleic acids comprising a PFP are introduced into the cells to screen for peptides capable of altering the phenotype of a cell.

By a "plurality of cells" herein is meant roughly from about $10^3$ cells to $10^8$ or $10^9$, with from $10^8$ to $10^8$ being preferred. This plurality of cells comprises a cellular library, wherein generally each cell within the library contains a member of the peptide molecular library, i.e., a different peptide (or nucleic acid encoding the peptide), although as will be appreciated by those in the art, some cells within the library may not contain a peptide, and some may contain more than species of peptide. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc. Thus, in a preferred embodiment, libraries of fusion polypeptides comprising PFPs and random peptides are made; that is, a library of random peptides is used to generate a library of fusion polypeptides (and thus a library of fusion polynucleotides encoding the fusion polypeptides).

In a preferred embodiment, the fusion nucleic acids encoding a bioactive peptide fused to PFPs are introduced into a first plurality of cells, and the effect of the encoded PFP fusion polypeptide is screened in a second or third plurality of cells, different from the first plurality of cells, i.e. generally a different cell type. That is, the effect of the bioactive peptide is due to an extracellular effect on a second cell; i.e. an endocrine or paracrine effect.

Thus, the methods of the present invention comprise introducing a molecular library of fusion nucleic acids encoding randomized peptides fused to a PFP into a plurality of cells. Each of the nucleic acids comprises a different nucleotide sequence encoding a random peptide fused to a PFP. The plurality of cells is then screened, as is more fully described below, for a cell exhibiting an altered phenotype, where the altered phenotype is due to the presence of a bioactive peptide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc. By "capable of altering the phenotype" herein is meant that the bioactive peptide can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the fusion nucleic acid was introduced; in other embodiments, the altered phenotype is detected in a second cell which is responding to some molecular signal from the first cell.

In a preferred embodiment, the altered phenotype of a cell indicates the presence of a bioactive peptide, acting in a transdominant way. By "transdominant" herein is meant that the bioactive peptide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions.

A transdominant effect upon a protein or molecular pathway is clearly distinguishable from randomization, change, or mutation of a sequence within a protein or molecule of known or unknown function to enhance or diminish a biochemical ability that protein or molecule already manifests. In a preferred embodiment, once a cell with an altered phenotype is detected, the presence of the PFP fusion polypeptide is verified, to ensure that the bioactive peptide was expressed and thus that the altered phenotype can be due to the presence of the bioactive peptide. As will be appreciated by those in the art, this verification of the presence of the bioactive peptide can be done either before, during or after the screening for an altered phenotype. This can be performed in a variety of ways known in the art, and preferably using methods that utilize FACS techniques.

Once the presence of the PFP fusion polypeptide is verified the methods of the present invention, the cell with the altered phenotype is generally isolated from the plurality which do not have altered phenotypes.

In a preferred embodiment, the fusion nucleic acid and/or the bioactive peptide (i.e. the fusion polypeptide) is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the fusion protein is isolated using a rescue sequence. Thus, for example, rescue sequences comprising epitope tags or purification sequences may be used to pull out the PFP fusion polypeptide using immunoprecipitation or affinity columns. In some instances, as is described below, this may also pull out the primary target molecule, if there is a sufficiently strong binding interaction between the bioactive peptide and the target molecule. Once rescued, the sequence of the bioactive peptide and/or fusion nucleic acid is determined. This information can then be used in a number of ways.

In a preferred embodiment, the bioactive peptide is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, either the bioactive peptide of the PFP fusion polypeptide or the fusion nucleic acid encoding it is used to identify target molecules, i.e. the molecules with which the bioactive peptide interacts. As will be appreciated by those in the art, there may be primary target molecules, to which the bioactive peptide binds or acts upon directly, and there may be secondary target molecules, which are part of the signalling pathway affected by the bioactive peptide; these might be termed "validated targets".

In a preferred embodiment, the bioactive peptide is used to pull out target molecules. Once primary target molecules have been identified, secondary target molecules may be identified in the same manner, using the primary target as the "bait". In this manner, signalling pathways may be elucidated. Similarly, bioactive peptides specific for secondary target molecules may also be discovered, to allow a number of bioactive peptides to act on a single pathway, for example for combination therapies.

PFP fusion polypeptides may be used in screening methods to screen a large number of cell types under a wide variety of conditions. Generally, the host cells are cells that are involved in disease states, and they are tested or screened under conditions that normally result in undesirable consequences on the cells. When a suitable bioactive peptide is found, the undesirable effect may be reduced or eliminated. Alternatively, normally desirable consequences may be reduced or eliminated, with an eye towards elucidating the cellular mechanisms associated with the disease state or signalling pathway. In this way, fusion polypeptides comprising PFPs and random peptides are made for screening of the random peptides for bioactivity.

In a preferred embodiment, the PFP can be used to evaluate, test and screen promoters. Thus, in this embodiment, the invention provides compositions comprising a promoter of interest and a gene encoding a PFP. Preferably the promoter is not the native PFP promoter.

In a preferred embodiment, the invention relates to methods that rely on a PFP gene fused to a promoter, such as an inducible promoterm that starts a signal cascade in the cell that ultimately results in a specific cellular response or biological activity (or modulation of that response or activity), as is generally described for IgE production in U.S. Ser. No. 09/076,624, hereby incorporated by reference in its entirety. In addition, these techniques allow individual cell assessment and thus are useful for high-throughput screening strategies, for example those that utilize fluorescence activated cell sorting (FACS) techniques, and thus allow screening of large numbers of compounds for their effects on IgE production.

Thus in a preferred embodiment the PFPs of the present invention provides a number of different constructs that allow for screening for antagonists and agonists of promoters. The methods comprise combining a candidate bioactive agent and a cell or a population of cells comprising a fusion nucleic acid. The cell or cells comprise a fusion nucleic acid. In a preferred embodiment, constructs comprising a promoter and two reporter genes can be made. In this embodiment, the first reporter gene is a PFP gene. The second reporter gene is another gene, e.g., a death gene that provides a nucleic acid that encodes a protein that causes the cells to die. A number of death genes/ligand pairs are known, including, but not limited to, the Fas receptor and Fas ligand (Bodmer, et al., "Characterization of Fas," J Biol Chem 272(30)18827–18833 (Jul. 25, 1997); muFAS, Gonzalez-Cuadrado, et al., "Agonistic anti-Fas Antibodies Induce Glomerular Cell Apoptosis in Mice In vivo," Kidney Int 51(6):1739–1746 (June 1997); Muruva, et al., Hum Gene Ther, 8(8):955 (May 1997)), (or anti-Fas receptor antibodies); p450 and cyclophosphamide (Chen, et al., "Potentiation of Cytochrome P450/Cyclophosphamide-Based Cancer Gene Therapy By Coexpression of the P450 Reductase Gene," Cancer Res 57(21):4830-4837 (Nov. 1, 1997)); thymidine kinase and gangcylovir (Stone, R., "Molecular 'surgery' For Brain Tumors," 256(5063):1513 (Jun. 12, 1992)), tumor necrosis factor (TNF) receptor and TNF.

In addition to inducible promoters, other promoters of interest can be used. For example, the promoter of interest can be either a constitutive promoter. As will be appreciated by those in the art, any number of possible promoters could be used. Suitable promoters of interest include, but are not limited to, inducible promoters such as IL-4 ε promoter, promoters that are induced by cytokines or growth factors such as the interferon responsive factors 1 to 4, NFkB (Fiering, et al., "Single Cell Assay of a Transcription Factor Reveals a Threshold in Transcription Activated By Signals Emanating From the T-Cell Antigen Receptor," Genes Dev 4(10):1823–1834 (October 1990)), promoters activated by heavy metals, heat shock promoters, stress promoters, etc.

When inducible promoters are used in this embodiment, suitable cell types are those that can be induced by the appropriate inducer, as will be appreciated by those in the art. Constitutive promoters are also of use, particularly tissue specific promoters, including, but not limited to, CNS, PNS, brain, kidney, skin, bone, lung, heart, liver, bladder, ovary, testes, colon, etc. specific promoters.

In a preferred embodiment, the inducible promoter is linked to a "one step" death gene, i.e., a death gene that upon a certain threshold expression, will kill a cell without requiring a ligand or secondary signal. In this embodiment, the inducible promoter is preferably "leaky", such that some small amount of death gene and a required secondary reporter gene such as a survival gene or a detection gene can be expressed. The cells that contain the death gene can then be selected on this basis, to avoid false positives. Once the presence of the construct is verified, candidate agents are added (and their presence preferably verified, using a detection or selection gene as well), and the promoter is induced. The population is then enriched for those cells that contain agents that inhibit the promoter, i.e. that will survive. In this embodiment, a PFP gene is used, particularly when inducible death genes are used. The use of a PFP gene allows cells to be sorted to give a population enriched for those containing the construct. As described above, a preferred embodiment uses "leaky" inducible promoters; that is, the cells are selected such that the IL-4 inducible promoter produces some PFP and death gene. In this embodiment, suitably "leaky" promoters are chosen such that some PFP is expressed (preferably enough to select the cells expressing the construct from those that are not), but not enough death gene is produced to cause death In a preferred embodiment, when two PFP reporter genes are used, they are fused together in such a way as to only require a single promoter, and thus some way of functionally separating the two genes is preferred. This can be done on the RNA level or the protein level. Preferred embodiments utilize either IRES sites (which allows the translation of two different genes on a single transcript (Kim, et al., "Construction of a Bifunctional mRNA in the Mouse By Using the Internal Ribosomal Entry Site of the Encephalomycarditis Virus," Molecular and Cellular Biology 12(8):3636–3643 (August 1992) and McBratney, et al., "The Sequence Context of the Initiation Codon in the Encephalomycarditis Virus Leader Modulates Efficiency of Internal Translation Initiation," Current Opinion in Cell Biology 5:961–965 (1993)), or a protease cleavage site (which cleaves a protein translation product into two proteins). Preferred protease cleavage sites include, but are not limited to, the 2a site (Ryan et al., J. Gen. Virol. 72:2727 (1991); Ryan et al., EMBO J. 13:928 (1994); Donnelly et al., J. Gen. Virol. 78:13 (1997); Hellen et al., Biochem, 28(26):9881 (1989); and Mattion et al., J. Virol. 70:8124 (1996), all of which are expressly incorporated by reference), prosequences of retroviral proteases including human immunodeficiency virus protease and sequences recognized and cleaved by trypsin (EP 578472, Takasuga et al., J. Biochem. 112(5)652 (1992)) factor Xa (Gardella et al., J. Biol. Chem. 265(26):15854 (1990), WO 9006370), collagenase (J03280893, Tajima et al., J. Ferment. Bioeng. 72(5):362 (1991), WO 9006370), clostripain (EP 578472), subtilisin (including mutant H64A subtilisin, Forsberg et al., J. Protein Chem. 10(5):517 (1991), chymosin, yeast KEX2 protease (Bourbonnais et al., J. Bio. Chem. 263(30):15342 (1988), thrombin (Forsberg et al., supra; Abath et al., BioTechniques 10(2):178 (1991)), *Staphylococcus aureus* V8 protease or similar endoproteinase-Glu-C to cleave after Glu residues (EP 578472, Ishizaki et al., Appl. Microbiol. Biotechnol. 36(4):483 (1992)), cleavage by NIa proteainase of tobacco etch virus (Parks et al ., Anal. Biochem. 216(2):413 (1994)), endoproteinase-Lys-C (U.S. Pat. No. 4,414,332) and endoproteinase-Asp-N, Neisseria type 2 IgA protease (Pohlner et al., Bio/Technology 10(7):799–804 (1992)), Protein Eng. 4(5):593 (1991)), enteropeptidase (WO 9006370), lysostaphin, a polyglycine specific endoproteinase (EP 316748), and the like. See e.g. Marston, F.A.O. (1986) Biol. Chem. J. 240, 1–12.

Thus, in preferred embodiment, fusion constructs comprising a gene of interest, an IRES site and an PFP gene are provided. In addition to the promoter of interest and a PFP gene, the fusion nucleic acids may comprise additional components, including, but not limited to, other reporter genes, protein cleavage sites, internal ribosome entry (IRES) sites, AP-1 sites, and other components as will be appreciated by those in the art.

In a preferred embodiment, foreign constructs comprising the inducible promoter and a PFP gene are made. By "foreign" herein is meant that the fusion nucleic acids originates outside of the cells. That is, a recombinant nucleic acid is made that contains an exogenous inducible promoter and a PFP gene. Thus, in some circumstances, the cells will contain both exogenous and endogenous inducible promoters. By "recombinant nucleic acid" herein is meant nucleic acid, originally formed in vitro, in general, by the manipulation of nucleic acid by endonucleases, in a form not normally found in nature. Thus an isolated nucleic acid, in a linear form, a nucleic acid containing components not normally joined, such as a non-PFP or non-PFP promoter and a PFP gene, or an expression vector formed in vitro by ligating DNA molecules that are not normally joined, are all considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

As for all the embodiments described herein, the recombinant nucleic acid (e.g. the fusion nucleic acids) may be introduced to a cell in a variety of ways, as will be appreciated by those in the art, including, but not limited to, $CaPO_4$ precipitation, liposome fusion, lipofectin®, electroporation, viral infection, etc. The constructs may preferably stably integrate into the genome of the host cell (for example, with retroviral introduction, described below), or may exist either transiently or stably in the cytoplasm (i.e. through the use of traditional plasmids, utilizing standard regulatory sequences, selection markers, etc.).

In a preferred embodiment, the exogeneous constructs, which may be in the form of an expression vector, are added as retroviral constructs, using techniques generally described in PCT US97/01019 and PCT US97/01048, both of which are expressly incorporated by reference in their entirety.

In a preferred embodiment, the fusion construct comprises an endogeneous promoter and an exogeneous PFP gene; "endogeneous" in this context means originating within the cell. That is, gene "knock-in" constructions are made, whereby an exogeneous PFP gene as described herein is added, via homologous recombination, to the genome, such that the reporter gene is under the control of the endogeneous promoter. This may be desirable to allow for the exploration and modulation of the full range of endogeneous regulation, i.e. regulatory elements (particularly those flanking the promoter) other than just the promoter fragment.

Homologous recombination may proceed in several ways. In one embodiment, traditional homologous recombination is done, with molecular biological techniques such as PCR being done to find the correct insertions. For example, gene "knock-ins" may be done as is known in the art, for example see Westphal et al., Current Biology 7:R530-R533 (1997), and references cited therein, all of which are expressly incorporated by reference. The use of recA mediated systems may also be done, see PCT US93/03868, hereby expressly incorporated by reference.

Alternatively, and preferably, the selection of the "knock ins" are done by FACS on the basis of the incorporation of a PFP gene. Thus, in a preferred embodiment, a first homologous recombination event is done to put a PFP gene, into at least one allele of the cell genome.

As will be appreciated by those in the art and described herein, any number of suitable cell types can be used in the present invention.

In a preferred embodiment, once a first endogeneous promoter has been combined with an exogeneous reporter construct, a second homologous recombination event may be done, preferably using a second reporter gene different from the first, to target the other allele of the cell genome, and tested as above.

Generally, induction of a PFP will indicate the correct placement of the PFP, which can be confirmed via sequencing such as PCR sequencing or Southern blot hybridization of the nucleic acid encoding the PFP. In addition, preferred embodiments utilize prescreening steps to remove "leaky" cells, i.e. those showing constitutive expression of the PFP.

Thus, in a preferred embodiment, the invention provides cell lines that contain fusion nucleic acids comprising an inducible promoter operably connected to nucleic acid encoding a PFP. Once made, the cell lines comprising these reporter constructs are used to screen candidate bioactive agents for the ability to modulate the production of a encoded protein operably linked to the promorter, as is described below.

As used herein, "candidate bioactive agent", "candidate agent", "exogeneous compound" or grammatical equivalents thereof, can be any molecule, e.g., protein, oligopeptide, small organic molecule, polysaccharide, or polynucleotide. PFPs can be operably linked or attached to a variety of candidate bioactive agents and used in the screening assays and methods of the present invention. Such candidate agents are describe more fully herein below.

In a preferred embodiment, the invention provides compositions and methods utilizing PFP as a reporter molecule for use in cell assays. As will be appreciated by those in the art, any assay for which a reporter gene can be used can be run using PFP.

In a preferred embodiment, the present invention provides compositions and methods utilizing a PFP and a chip device comprising integrated photodetectors at individual loci. The method may be practiced with any suitable chip device that includes an electronic circuit capable of reading the sensed signal generated by each photodetector and generating output data signals therefrom. The output data signals are indicative of the light emitted, due to the presence of a PFP, at the various loci. As will be appreciated by those in the art, any assay that evaluates binding interactions can utilize the present invention.

Thus, the present invention finds use in a variety of assays, including but not limited to, assays for protein-protein interactions, protein-nucleic acid interactions, and nucleic acid-nucleic acid interactions.

In a preferred embodiment, any cellular assay that evaluates the effects of candidate agents, preferably either nucleic acids or proteins (including peptide), can utilize the present invention. In this embodiment, the candidate agents are fused to the PFPs of the present invention, generally through making fusion nucleic acids and transforming into the cells to be assayed under conditions that allow expression (if peptides are used) of the candidate agent. This allows a confirmation that the candidate agent has been expressed, as well as tracking and localization of the candidate agent, and the ability to sort cells comprising the candidate agents.

Thus, the present invention finds use in a variety of cellular assays, including but not limited to, assays for alterations in exocytosis, cell cycle regulation, apoptosis, cellular proliferation and/or differentiation, etc. The cells screened can also be a variety of cell types, including, but not limited to, any cells described herein, including mast cells, T cells, B cells, macrophages, adipocytes, smooth muscle cells, etc.

In addition, as described herein, the PFPs of the invention find particular use in screening assays that require a reporter protein.

The present invention is directed to the detection of alterations in cellular phenotypes, such as cell cycle regulation, exocytosis, small molecule toxicity, cell surface receptor expression, enzyme expression, etc. by evaluating or assaying a variety of cellular parameters, generally through the use of a fluorescence-activated cell sorter (FACS) machine. There are a number of parameters that can be measured to allow detection of alterations in a variety of cellular phenotypes as is more fully described below. By assaying a plurality of these parameters either sequentially or preferably simultaneously, rapid and accurate screening may be done.

In a preferred embodiment, the methods described herein are used to screen for modulators of cellular phenotypes. Cellular phenotypes that may be assayed include, but are not limited to, cellular apoptosis, including cell cycle regulation, exocytosis, toxicity to small molecules, the expression of any number of moieties including receptors (particularly cell surface receptors), adhesion molecules, cytokine secretion, protein-protein interactions, etc. As will be appreciated by those in the art, any number of cellular assays that rely on a PFP can be developed. Thus, in a preferred embodiment, the invention provides methods of screening comprising providing cell lines comprising nucleic acids encoding a PFP, adding candidate bioactive agents and detecting changes in chellular phenotype. The nucleic acid may preferably be a fusion nucleic acid, encoding a gene or regulatory element of interest operably linked to a PFP.

In a preferred embodiment, the methods are used to evaluate cell cycle regulation. In this embodiment, preferred cellular parameters or assays are cell viability assays, assays to determine whether cells are arrested at a particular cell cycle stage ("cell proliferation assays"), and assays to determine at which cell stage the cells have arrested ("cell phase assays"). By assaying or measuring one or more of these parameters, it is possible to detect not only alterations in cell cycle regulation, but alterations of different steps of the cell cycle regulation pathway. This may be done to evaluate native cells, for example to quantify the aggressiveness of a tumor cell type, or to evaluate the effect of candidate drug agents that are being tested for their effect on cell cycle regulation. In this manner, rapid, accurate screening of candidate agents may be performed to identify agents that modulate cell cycle regulation.

Thus, the present methods are useful to elucidate bioactive agents that can cause a population of cells to either move out of one growth phase and into another, or arrest in a growth phase. In some embodiments, the cells are arrested in a particular growth phase, and it is desirable to either get them out of that phase or into a new phase. Alternatively, it may be desirable to force a cell to arrest in a phase, for example G1, rather than continue to move through the cell cycle. Similarly, it may be desirable in some circumstances to accelerate a non-arrested but slowly moving population of cells into either the next phase or just through the cell cycle, or to delay the onset of the next phase. For example, it may be possible to alter the activities of certain enzymes, for example kinases, phosphatases, proteases or ubiquitination enzymes, that contribute to initiating cell phase changes.

In a preferred embodiment, the methods described herein are done on cells that are not arrested in the G1 phase; that is, they are rapidly or uncontrollably growing and replicating, such as tumor cells. In this manner, candidate agents are evaluated to find agents that can alter the cell cycle regulation, i.e. cause the cells to arrest at cell cycle checkpoints, such as in G1 (although arresting in other phases such as S, G2 or M are also desirable). Alternatively, candidate agents are evaluated to find agents that can cause proliferation of a population of cells, i.e. that allow cells that are generally arrested in G1 to start proliferating again; for example, peripheral blood cells, terminally differentiated cells, stem cells in culture, etc.

Accordingly, in a preferred embodiment, the invention provides methods for screening for alterations in cell cycle regulation of a population of cells. "Alteration" and "modulation" (used herein interchangeably), as used herein can include both increases and decreases in the parameter or phenotype being measured. By "alteration" or "modulation" in the context of cell cycle regulation, is generally meant one of two things. In a preferred embodiment, the alteration results in a change in the cell cycle of a cell, i.e. a proliferating cell arrests in any one of the phases, or an arrested cell moves out of its arrested phase and starts the cell cycle, as compared to another cell or in the same cell under different conditions. Alternatively, the progress of a cell through any particular phase may be altered; that is, there may be an acceleration or delay in the length of time it takes for the cells to move thorough a particular growth phase. For example, the cell may be normally undergo a G1 phase of several hours; the addition of an agent may prolong the G1 phase.

The measurements can be determined wherein all of the conditions are the same for each measurement, or under various conditions, with or without bioactive agents, or at different stages of the cell cycle process. For example, a measurement of cell cycle regulation can be determined in a cell population wherein a candidate bioactive agent is present and wherein the candidate bioactive agent is absent. In another example, the measurements of cell cycle regulation are determined wherein the condition or environment of the populations of cells differ from one another. For example, the cells may be evaluated in the presence or absence of physiological signals, for example hormones, antibodies, peptides, antigens, cytokines, growth factors, action potentials, pharmacological agents (i.e. chemotherapeutics, etc.), or other cells (i.e. cell-cell contacts). In another example, the measurements of cell cycle regulation are determined at different stages of the cell cycle process. In yet another example, the measurements of cell cycle regulation are taken wherein the conditions are the same, and the alterations are between one cell or cell population and another cell or cell population.

In a preferred embodiment, the candidate bioactive agents are peptides and are fused with PFPs; fusion nucleic acids are made, transformed into the cells and expressed. The presence of a signal from the PFP shows that the candidate agent is expressed. The cells can then be screened as below, to detect agents that effect cell viability, etc.

By a "population of cells" or "library of cells" or "plurality of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines (particularly when, as described below. The cells may be in any cell phase, either synchronously or not, including M, G1, S, and G2. In a preferred embodiment, cells that are replicating or proliferating are used; this may allow the use of retroviral vectors for the introduction of candidate bioactive agents fused to a PFP. Alternatively, non-replicating cells may be used, and other vectors (such as adenovirus and lentivirus vectors) can be used. In addition, although not required, the cells are compatible with dyes and antibodies.

Preferred cell types for use in the invention will vary with the cellular phenotype to be modulated. Suitable cells include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc. As described below, additional cell types may be used for screening for exocytosis.

In a preferred embodiment, the cell cycle regulation methods comprise sorting the cells in a FACS machine by assaying several different cell parameters, including, but not limited to, cell viability, cell proliferation, and cell phase.

In a preferred embodiment, cell viability is assayed, to ensure that a lack of cellular change is due to experimental conditions (i.e. the introduction of a candidate bioactive agent) not cell death. There are a variety of suitable cell viability assays which can be used, including, but not limited to, light scattering, viability dye staining, and exclusion dye staining.

In a preferred embodiment, a light scattering assay is used as the viability assay, as is well known in the art. When viewed in the FACS, cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90/scatter; similarly, membrane blebbing can alter the forward scatter. Alterations in the intensity of light scattering, or the cell-refractive index indicate alterations in viability.

In a preferred embodiment, the cell phase assay is a cyclin destruction assay. In this embodiment, prior to screening (and generally prior to the introduction of a candidate bioactive agent, as described below), a fusion nucleic acid is introduced to the cells. The fusion nucleic acid comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a PFP, the presence or absence of the PFP can be detected as described herein and can serve to identify the cell phase of the cell population. In a preferred embodiment, multiple boxes are used, preferably each with a different fluorophore, such that detection of the cell phase can occur.

A number of cyclin destruction boxes are known in the art, for example, cyclin A has a destruction box comprising the sequence RTVLGVIGD (SEQ. ID NO:45); the destruction box of cyclin B1 comprises the sequence RTALGDIGN (SEQ. ID NO:36). See Glotzer et al., Nature 349:132–138 (1991). Other destruction boxes are known as well: YMTVSIIDRFMQDSCVPKKMLQLVGVT (SEQ. ID NO:46; rat cyclin B); KFRLLQETMYMTVSIIDRFMQN-SCVPKK (SEQ. ID NO:47; mouse cyclin B); RAILID-WLIQVQMKFRLLQETMYMTVS (SEQ. ID NO:48; mouse cyclin B1); DRFLQAQLVCRKKLQWGI-TALLLASK (SEQ. ID NO:49; mouse cyclin B2); and MSVLRGKLQLVGTMMLL (SEQ. ID NO:50; mouse cyclin A2).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a PFP.

Accordingly, the results of sorting after cell phase assays generally result in at least two populations of cells that are in different cell phases.

In a preferred embodiment, the methods of the present invention can be used to screen candidate bioactive agents for the ability to modulate cell cycle regulation, including the activation or suppression of cell cycle checkpoint pathways and ameliorating checkpoint defects. The candidate bioactive agent, fused to a PFP, can be added to the cell population exogenously or can be introduced into the cells as described further herein.

In a preferred embodiment, the methods are used to screen candidate bioactive agents for the ability to modulate cell cycle regulation, including the activation or suppression of cell cycle checkpoint pathways and ameliorating checkpoint defects. The candidate bioactive agent, fused to a PFP, can be added to the cell population exogenously or can be introduced into the cells as described further herein.

In a preferred embodiment, when the candidate agent is introduced to the cells using a viral vector, the candidate peptide agent is linked to an PFP gene, and the methods of the invention include at least one expression assay. An expression assay is an assay that allows the determination of whether a candidate bioactive agent has been expressed, i.e. whether a candidate peptide agent is present in the cell. Thus, by linking the expression of a candidate agent to the expression of PFP, the presence or absence of the candidate peptide agent may be determined. Accordingly, in this embodiment, the candidate agent is operably linked to a detectable molecule. Generally, this is done by creating a fusion nucleic acid. The fusion nucleic acid comprises a first nucleic acid encoding the candidate bioactive agent (which can include fusion partners, as described above), and a second nucleic acid encoding a detectable molecule. The terms "first" and "second" are not meant to confer an orientation of the sequences with respect to 5'-3' orientation of the fusion nucleic acid. For example, assuming a 5'-3' orientation of the fusion sequence, the first nucleic acid may be located either 5' to the second nucleic acid, or 3' to the second nucleic acid. Preferred detectable molecules in this embodiment include, but are not limited to, PFP.

In general, the candidate agents are added to the cells (either extracellularly or intracellularly, as described above) under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

A variety of other reagents may be included in the assays. These include reagents like salts, neutral proteins, e.g. albumin, detergents, etc which may be used to facilitate optimal protein-protein binding and/or reduce non☐specific or background interactions. Also reagents that otherwise improve the efficiency of the assay, such as protease inhibitors, nuclease inhibitors, anti-microbial agents, etc., may be used. The mixture of components may be added in any order that provides for detection. Washing or rinsing the cells will be done as will be appreciated by those in the art at different times, and may include the use of filtration and centrifugation. When second labeling moieties (also referred to herein as "secondary labels") are used, they are preferably added after excess non-bound target molecules are removed, in order to reduce non-specific binding; however, under some circumstances, all the components may be added simultaneously.

In a preferred embodiment, the cells are sorted using fluorescent-activated cell sorting (FACS). In the invention herein, cell cycle regulation is evaluated by multiple parameters which results in reduced background and greater specificity. In contrast, FACS has been used in the past to evaluate two different or unrelated characteristics at the same time which identifies cells having those two characteristics, but does not reduce the background for the combined characteristics.

Thus, the cells are sorted or enriched in a FACS on the basis of one or more of the assays, including a cell viability assay, a proliferation assay, a cell phase assay, and (when candidate agents are expressed with detectable moieties) an expression assay. The results from one or more of these assays are compared to cells that were not exposed to the candidate bioactive agent, or to the same cells prior to introduction of the candidate agent. Alterations in these results can indicate that the agent modulates cell cycle regulation.

A strength of the present invention is that a library of candidate agents may be tested in a library of cells, because the present methods allow single cell sorting, with extremely high specificity, such that very rare events may be detected. The use of multiple laser paths allows sort accuracy of 1 in 106 with better than 70% accuracy.

In addition, the present invention can, in addition to the identification of multiple cell cycle regulation properties, be combined with the identification of other cellular characteristics. For example, parameters of general cellular health can be determined and selected for by using i.e., dye Indo-1 indicating a calcium response. Other cellular parameters which are routinely identified by the skilled artisan include but are not limited to: cell size, cell shape, redox state, DNA content, nucleic acid sequence, chromatin structure, RNA content, total protein, antigens, lipids, surface proteins, intracellular receptors, oxidative metabolism, DNA synthesis and degradation and intracellular pH.

In a preferred embodiment, each of the measurements is determined simultaneously from an individual cell as it passes through the beam paths of multiple lasers. Alternatively, the measurements are done sequentially. By using more than one parameter to detect cell cycle regulation or alterations in cell cycle regulation, background is reduced and specificity is increased. The cells meeting the parameters of the desired properties can be physically sorted from cells not meeting the desired parameters or they can be identified by their percentage in the cell population.

In general, KD s of <1 $\mu$M are preferred, to allow for retention of binding in the presence of the shear forces present in FACS sorting. In a preferred embodiment, the cells are sorted at very high speeds, for example greater than about 5,000 sorting events per sec, with greater than about 10,000 sorting events per sec being preferred, and greater than about 25,000 sorting events per second being particularly preferred, with speeds of greater than about 50,000 to 100,000 being especially preferred.

Cells processed for stimulation and staining are generally taken up in buffer and filtered prior to cytometry. Cells can be analyzed using a FACSCAN (Becton Dickinson Inc., laser line 488 nm) or a Mo-Flo (Cytomation, Inc., laser lines 350 nm broadband (UV), 488 nm, and 647 nm) Cytometer. Cells are sorted, if desired, using the Mo-Flo.

Wherein the cells are analyzed by microscopy, cells post stimulation or staining are generally mounted onto glass slides and coverslipped and visualized as described above. In one example, the cells are directly visualized by brightfield and fluorescence microscopy on an inverted microscope (i.e., TE300, Nikon) using standard filter sets. Images can also be obtained using an inverted confocal scanning microscope (Zeiss, Inc., Bio-Rad, Inc.) using standard filter sets.

The sorting results in a population of cells having the desired properties. In a preferred embodiment, the parameters are set to identify at least one candidate bioactive agent that modulates cell cycle regulation.

In a preferred embodiment, the bioactive agent is characterized. This will proceed as will be appreciated by those in the art, and generally includes an analysis of the structure, identity, binding affinity and function of the agent. Generally, once identified, the bioactive agent is resynthesized and combined with the target cell to verify the cell cycle regulation modulation under various conditions and in the presence or absence of other various agents. The bioactive can be prepared in a therapeutically effective amount to modulate cell cycle regulation and combined with a suitable pharmaceutical carrier.

In a preferred embodiment, the cell populations can be subjected to various experimental conditions, with and without the candidate agents. Changes in conditions include but are not limited to changes in pH, temperature, buffer or salt concentration, etc. In a preferred embodiment, the pH is changed, generally by increasing or decreasing the pH, usually by from about 0.5 to about 3 pH units. Alternatively, the temperature is altered, with increases or decreases of from about 5° C. to about 30° C. being preferred. Similarly, the salt concentration may be modified, with increases or decreases of from about 0.1 M to about 2 M being preferred.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, or segregation, isolation steps. Moreover, it is understood that in some cases detection is in the cells, but can also take place in the media, or vice versa.

In a preferred embodiment, the invention provides methods for screening for alterations in exocytosis of a population of cells. By "alteration" or "modulation" in the context of exocytosis is meant a decrease or an increase in the amount of exocytosis in one cell compared to another cell or in the same cell under different conditions. The measurements can be determined wherein all of the conditions are the same for each measurement, or under various conditions, with or without bioactive agents, or at different stages of the exocytic process. For example, a measurement of exocytosis can be determined in a cell population wherein a candidate bioactive agent fused to PFP is present or is absent. In another example, the measurements of exocytosis are determined wherein the condition or environment of the populations of cells differ from one another. For example, the cells may be evaluated in the presence or absence of physiological signals, such as exocytic inducers (i.e, $Ca^{++}$, ionomycin, etc.), hormones, antibodies, peptides, antigens, cytokines, growth factors, action potentials, or other cells (i.e. cell-cell contacts). In another example, the measurements of exocytosis are determined at different stages of the exocytic process. In yet another example, the measurements of exocytosis are taken wherein the conditions are the same, and the alterations are between one cell or cell population and another cell or cell population.

By a "population of cells" herein is meant a sample of cells as defined above. In this embodiment, the cells are preferably (but not required) to be rapidly growing, retrovirally infectable, and compatible with dyes and antibodies. Preferred cell types for use in this embodiment, include, but are not limited to, mast cells, neurons, adrenal chromaffin cells, basophils, endocrine cells including pancreatic β-cells, pancreatic acinar cells including exocrine cells, neutrophils, monocytes, lymphocytes, mammary cells, sperm, egg cells and PMN leukocytes, endothelial cells, adipocytes, and muscle cells.

In a preferred embodiment, changes in light scattering are assayed to determine alterations in exocytosis in a population of cells. General methodologies for light scattering measurements are further described in Perretti, et al., J. Pharmacol. Methods, 23(3): 187–194 (1990) and Hide et al., J. Cell Biol., 123(3):585–593 (1993), both incorporated herein by reference. In general, changes of at least about 5% from baseline are preferred, with at least about 25% being more preferred, at least about 50% being particularly preferred, and at least about 75 to 100% being especially preferred. Baseline in this case generally means the light scatter properties of the cells prior to exocytotic stimulation. In each case provided herein, the baseline may also be set for any control parameter. For example, the baseline may be set at the exocytosis measurement of a particular cell, a similar cell under different conditions, or at a particular time point during exocytosis.

In another preferred embodiment, changes in surface granule enzyme activity is determined. Secretory granules contain enzymes such as proteases and glycosidases which are released as part of the exocytic process. Frequently, these enzymes are inactive within the granule, due to the low pH, but upon exposure to the extracellular media at physiological pH, they become activated. These enzyme activities can be measured using chromogenic or fluorogenic substrates as components of the extracellular media. The substrates can be PFP fusion polypeptides having a cleavable enzyme site. This allows detection of exocytic cells in varying approaches.

In one embodiment, sometimes called herein the population based enzyme assay, the generation of signal via cleavage of a chromogenic or fluorogenic substrate can be quantified in the media. That is, the amount of detectable reaction product in the media is related to the amount of enzyme present, and thus to the amount of exocytosis. In this embodiment, it is the media, not the cells, that becomes detectable.

In a preferred embodiment, cells are subjected to an exocytic stimulus, and optionally, a candidate bioactive agent. A PFP fusion polypeptide comprising a cleavalable enzyme substrate is added to the media, and changes in the signal are evaluated, as the enzymes cleave the extracellular substrates.

In an alternate preferred embodiment, sometimes called herein "in situ enzymology assay", fluorogenic substrates that precipitate upon cleavage are used. That is, upon exocytosis a considerable amount of enzyme activity remains cell/granule associated and can be visualized using fluorescent substrates which precipitate at the site of activity. For example, substrates for glucuronidase, such as ELF-97 glucuronide, precipitate on exocytosing cells, but not resting cells, and thus the cells can show increased fluorescence. The fluorescence is a direct measurement of exocytosis and is pH dependent reflecting the pH optima of the exocytosed enzyme. This method also provides a method of distinguishing different subtypes of granules based on their enzyme profile.

In a preferred embodiment, the cell population is subjected to an exocytic stimulus and then incubated with a PFP fusion polypeptide having a cleavable enzyme substrate. A candidate bioactive agent is optionally added. The cells are washed and then viewed in the microscope or flowcytometer.

Preferred granule enzymes include but are not limited to chymase, tryptase, arylsulfatase A, beta-hexosaminidase, beta-glucuronidase, and beta D-galactosidase. Substrates includes ELF-97 glucuronide, N-acetyl beta-D glucoronide, ELF-97 coupled to peptides, etc., many of which are commercially available, i.e., from Molecular Probes, supra, particular Chapter 10, more particularly Section 2 of Chapter 10, and referenced "related chapters".

In a preferred embodiment, the substrate comprises a detectable molecule formed of a PFP and a second fluorescent protein having fluorescent properties such that when in close proximity allow fluorescence resonance energy transfer (FRET). That is, the excitation spectra of a PFP overlaps the emission spectra of a second fluorescent protein (where the second protein may be a second PFP with a different but overlapping emission spectra from the first or other PFP). Accordingly, exciting the PFP results in emission by the second protein. If a protease cleavage site is engineered between the PFP and the second protein to form a "FRET construct", upon exposure of the FRET construct to an active protease which cleaves the construct, the PFP and second protein separate. Accordingly, exciting the PFP can result in the second protein emission or, alternatively, the loss of emission by the second protein.

Preferably, the protease dependent cleavage site inserted between a PFP and a second fluoroscent protein of the FRET construct is specific for a granule specific enzyme. Thus, the FRET construct can be used for detecting granule specific proteases specific for the cleavage site of the FRET construct. In this embodiment, the protease substrate that is combined with the cells or media includes the FRET construct. The FRET system allows for detection of the detectable molecule in its cleaved and uncleaved state, and distinguishes between the two. The system is further described in Xu et al., Nucleic Acid Res. 26(8):2034 (1998); and Miyawaki et al., Nature 388(6645):882–887 (1997), both of which are incorporated by reference.

The amount of substrate added to the cells or media will depend in part on the enzyme's specific activity and the substrate itself, but generally is about 250 nm to about 1 mM, from about 1 $\mu$M to about 100 $\mu$M being preferred, and from about 1 $\mu$M to about 10 $\mu$M being particularly preferred. In general, changes of at least about 5% from baseline are preferred, with at least about 25% being preferred, at least about 100% being particularly preferred and at least about 100% being especially preferred. Baseline in this case means the amount of substrate cleavage prior to induction of exocytosis.

In a preferred embodiment, changes in the quantity of granule specific proteins are determined. Secretory granules contain proteins which are specifically targeted to the granule compartment due to specific properties of these proteins. Upon exocytic induction, the granule specific proteins are exposed to the surface and detected.

In a preferred embodiment, detectable granule specific proteins fused to a PFP are combined with a population of cells and subjected to conditions known to induce exocytosis. Optionally, a bioactive candidate fused to PFP is combined with the cell population and detectable granule specific protein and the granule specific protein is detected. Granule specific proteins include but are not limited to VAMP and synaptotagmin. Also included within the definition of granule specific proteins are the mediators released during exocytosis, including, but not limited to, serotonin, histamine, heparin, hormones, etc.

The fusion proteins can be constructed by ligating the nucleic acids encoding the granule specific protein with a nucleic acid encoding a PFP which allows a cell or compound comprising the PFP to be distinguished from one that does not contain it, i.e., an epitope, sometimes called an antigen TAG, or a fluorescent molecule. These constructs can be made in such a way so that upon exocytosis an epitope, internal to the granule, is exposed at the cell surface and can then be detected. The epitope is preferably any detectable peptide which is not generally found on the cytoplasmic membrane, although in some instances, if the epitope is one normally found on the cells, increases may be detected, although this is generally not preferred.

In a preferred embodiment, the cell population containing the detectable granule specific protein fused to a PFP is subjected to exocytic conditions. Optionally, a candidate bioactive agent and/or exocytic inhibitor is included. Preferably, the cells are washed. Fluorescence of the PFP fusion polypeptide is detected on the cells. In general, changes of at least about 5% from baseline are preferred, with at least about 25% being more preferred, at least about 50% being particularly preferred and at least about 100% being especially preferred. Generally, baseline in this case means amount of fluorescence prior to exocytic stimulus.

In the invention herein, the same characteristic of exocytosis is evaluated by multiple parameters which results in reduced background and greater specificity. In contrast, FACS has been used in the past to evaluate two different or unrelated characteristics at the same time which identifies cells having those two characteristics, but does not reduce the background for the combined characteristics. The present invention can, however, in addition to the identification of multiple exocytosis properties, be combined with the identification of other cellular parameters, as described above.

In a preferred embodiment, the methods are used to screen candidate bioactive agents for the ability to modulate exocytosis. The candidate bioactive agents may be combined with the cell population before, during or after exocytosis is stimulated, preferably before. In some instances, it may be desirable to determine the effect of the candidate bioactive agent, also referred to as "candidate agents" herein, on the cell wherein exocytosis is not induced or wherein exocytosis is inhibited. The candidate bioactive agent can be added to the cell population exogenously or can be introduced into the cells as described further herein.

In a preferred embodiment, as above for cell cycle assays, a library of different candidate bioactive agents are used.

Wherein the candidate agents are nucleic acids, methods known in the art such as calcium phosphate, electroporation, and injection may be used to introduce these to the cells. The exocytic stimulus is generally combined with the cells under physiological conditions. Incubations may be performed at any temperature which facilitates optimal activity, typically between 4 and 40° C. Incubation periods are selected for optimum activity, but may also be optimized to facilitate rapid high through put screening.

As above, a variety of other reagents may be included in the assays, and the cells are sorted as above. The sorting results in a population of cells having the desired exocytic properties. In a preferred embodiment, the parameters are set to identify at least one candidate bioactive agent that modulates exocytosis.

In a preferred embodiment, the bioactive agent is characterized. This will proceed as will be appreciated by those in the art, and generally includes an analysis of the structure, identity, binding affinity and function of the agent. Generally, once identified, the bioactive agent is resynthesized and combined with the target cell to verify the exocytosis modulation under various conditions and in the presence or absence of other various agents. The bioactive can be prepared in a therapeutically effective amount to modulate exocytosis and combined with a suitable pharmaceutical carrier.

In a preferred embodiment, the cellular phenotype to be modulated is small molecule (or other candidate agent) toxicity. These are generally as described above for cell viability assays. Small molecule dose responses can also be compared by comparing the cells with the greatest functional response, and then backgating to see if there is more or less toxicity associated with those cells.

In a preferred embodiment, the cellular phenotype involves the expression or activity of cell surface receptors; up to sixteen cell surface markers may be followed simultaneously, with up to eight being preferred. The presence or absence of any particular cell surface marker can be detected by directly and indirectly conjugated antibodies against any cell surface protein whose cell surface expression reflects an important functional parameter associated with the cells being studied. The effect of candidate agents such as small molecules can then be tested against individual or multiple markers.

In a preferred embodiment, the cellular phenotype involves the expression or activity of enzymes such as fluorescent based reporter systems that can report a biological event that occurs simultaneously with the primary measurement or is a result of the primary measurement. This reporter system can be a readout of upstream signal transduction pathways that are active in the cytoplasm, or of nuclear transcriptional or translational events, as well as export events from the nucleus or the cell.

In a preferred embodiment, the cellular phenotype involves protein-protein interactions (or interactions between other binding ligands), such as dimerizatioh, that can be either disrupted or instigated by a candidate agent. These events may be measured by the appearance or disappearance of FRET between two labeled binding ligands.

Candidate agents useful in the methods and compositions of the present invention are described below.

Candidate bioactive agents (or "candidate agents") encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is described above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as described below nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al, Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eucaryotic genomes may be used as is described above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of 107–108 different antibodies provides at least one combination with sufficient affinity to interact with most potential antigens faced by an organism. Published in vitro selection techniques have also shown that a library size of 107 to 108 is sufficient to find structures with affinity for the target. A library of all combinations of a peptide 7 to 20 amino acids in length, such as generally proposed herein, has the potential to code for 207 (109) to 2020 . Thus, with libraries of 107 to 108 different molecules the present methods allow a "working" subset of a theoretically complete interaction library for 7 amino acids, and a subset of shapes for the 2020 library. Thus, in a preferred embodiment, at least 106, preferably at least 107, more preferably at least 108 and most preferably at least 109 different sequences are simultaneously analyzed in the subject methods. Preferred methods maximize library size and diversity.

The candidate bioactive agents are combined or added to a cell or population of cells. Suitable cell types for different embodiments are described above. By "population of cells" herein is meant at least two cells, with at least about 105 being preferred, at least about 106 being particularly preferred, and at least about 107, 108 and 109 being especially preferred.

The candidate bioactive agent and the cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

In a preferred embodiment, the candidate bioactive agents are either nucleic acids or proteins (proteins in this context includes proteins, oligopeptides, and peptides) that are introduced into the host cells using retroviral vectors, as is generally described in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the ψ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

In a preferred embodiment, the candidate bioactive agents are linked to a fusion partner as defined above.

Generally a plurality of assay mixtures can be run in parallel with different agent concentrations to obtain a differential response to the various concentrations. Typically, one of these concentrations serves as a negative control, i.e., at zero concentration or below the level of detection.

The following Examples are illustrative of the disclosed composition and methods, and do not serve to limit the scope of the invention. From the description herein, the essential characteristics of the present invention can be ascertained. Without departing from the spirit and scope thereof, various changes and modifications of the invention will be clear to one skilled in the art and can be made to adapt the invention to various usages and conditions. Thus, other embodiments are also within the claims.

EXAMPLES

Example 1

Fresh samples of *Physalia utriculus* (*P. utriculus*) were collected at dawn along Kailua Beach, a windward beach of Oahu, Hi. The samples were transported in sea water and examined within 2 hours of collection by light microscopy (FIG. 1) and fluorescent microscopy (FIG. 2) using an Oympus IX-70 microscope. The fluorescent microscopy was performed using the following fluorescent filter cube sets ("EX" is excitation and "EM" is emission):

| | | |
|---|---|---|
| Ultra Violet (UV) Wide: | EX 330–385 | EM 400–420 |
| Wide Blue: | EX 450–480 | EM 500–515 |
| Wide Green: | EX 480–550 | EM 570–590 |

An intense red fluorophore was observed in tissue from a fresh sample of tentacle of *P. uticulus* with the Wide Green cube set (see FIG. 2).

Example 2

Fresh samples of *P. utriculus* were collected as described above. A protein extract was then prepared from a tentacle of the fresh *P. utriculus* sample. The proteins in the extract were analyzed by polyacrylamide gel electrophoresis (PAGE). Specifically, aliquots of the protein extract were loaded onto a denaturing SDS polyacrylamide gel (FIG. 3A) and onto a native polyacrylamide gel (FIG. 3B). Molecular weight standards were separately loaded onto each gel. The proteins in the aliquot and the molecular weight standards were then resolved by PAGE.

The SDS polyacrylamide gel was then silver stained. The protein products resolved via PAGE were then subjected to light or fluorescent microscopy using a Wide Green filter cube set (Olympus IX-70). In this manner, two protein gel bands of approximately 12 kD and 37 kD were detected in both the native and the denaturing SDS polyacrylamide gel (FIGS. 3A and 3B). However, fluorescent activity was detected only in the two protein gel bands in the native gel (FIG. 3B), and not in the denaturing gel (FIG. 3A). In this manner, PFPs having a molecular weigh of approximately 12 kD and 37 kD and fluorescent activity were detected. The fluorescent 12 kD and 37 kD protein gel bands in the native gel were excised from the gel (FIGS. 3B and 3C) and the proteins extracted for sequencing, as described below.

Using this approach PFPs were detected using the Wide Green Filter set. However, additional PFPs can be detected using other filter sets. For example, other PFPs can be detected using filter cube sets designed according to the observed PFP excitation and emission spectra described herein and in Example 4 below.

Example 3

Protein extract from a tentacle of a fresh *P. utriculus* sample was prepared; the proteins in the extract were resolved by native PAGE, and the resolved proteins detected, as described above (FIG. 3A-C). The resulting protein gel bands were then excised from the gel and the proteins extracted from the gel slices. Aliquots of the extracted proteins were then provided to the University of Hawaii Biotechnology Sequencing Facility (BSF) for sequencing.

The proteins were then sequenced from the N-terminus according to the Applied Biosystems Procise™ Protein Sequencing Protocol in the User's Manual Set, incorporated herein in its entirety. Amino acid sequences obtained from these sequencing reactions include the following:

| | |
|---|---|
| ALPGAIGKLGLAGLQG | SEQ ID NO:51 |
| GLDESAGILFPSINLI | SEQ ID NO:52 |
| GLDGAHDLFGAEGMAV | SEQ ID NO:53 |
| APDGNPGKVGPSIVVG | SEQ ID NO:54 |
| GLEGNPGKFGIPGYKV | SEQ ID NO:55 |
| TIPKDAKLVGLRFVTV | SEQ ID NO:56 |
| TLDDDLQLDVLIIVDE | SEQ ID NO:57 |
| GIPVDFKFIGKRIQNQ | SEQ ID NO:58 |

Example 4

In order to further assess the fluorescent properties of PFPs, fresh animals were collected and systematic fluorescence scans were performed (see FIGS. 4, 5, and 6). Specifically, samples of living *Physalia* were collected and tentacles excised therefrom for fluorescent excitation and emission determination using a double monochromator, Cary Eclipse Varian Spectrophotometer. Approximately 100 µl wet volume of tentacle was added to 100 µl sea water in a 96 well black plate. The excitation-emission sets that were detected are described in Table 2 below.

TABLE 2

Fluorescence Characterization by Double Monochromator Scanning of Excitation and Emission Spectra from 200 to 1100 nm (+/−5 nm)

| FIG. Number | Emmission Scans (nm +/− 5 nm) | | Excitation Scans (nm +/− 5 nm) | |
|---|---|---|---|---|
| | Excitation Set At | Emissions Observed | Emission Set At | Excitation Observed |
| 5A | | | 600 | 222, 301 |
| 6 | | | 456 | 221 |
| 6 | | | 838 | 421 |
| 5B | | | 898 | 301, 451 |
| 6 | | | 597 | 301 |
| 6 | | | 421 | 222 |
| 6 | 222 | 421 | | |
| 4A, 4B | 301 | 598, 888–898 | | |
| 6 | 421 | 838 | | |
| 6 | 450 | 900 | | |
| Reference Compounds (nm) | | | | |
| Chlorophyll | 435 | 645 | | |
| GFP | 395 | 509 | | |

In summary, PFPs exhibit several unique and valuable properties as demonstrated herein. There is an unprecedented broad band-width of the excitation spectrum. For example, PFPs of the present invention can exhibit an excitation wavelength in a range from about 210 nm to about 550 nm, as compared to known fluorescent proteins. More specifically, PFPs of the present invention exhibit several unique and valuable properties which include, but are not limited to: 1) a dramatic excitation emission wavelength set of 301 nm excitation and 598 nm emission; 2) excitation emission wavelength sets that overlap and span from 220 nm to 898 nm; and far-red emission resulting from an excitation wavelength of 456 nm and 301 nm. The 898 nm emission peak is unprecented as compared to other known fluorescent proteins. The highest wavelength emission of a known fluorescent protein has an emission wavelength of 716 nm with excitation wavelength at 414 nm (see, e.g., emission spectra at the Web page at RH-414 Bio-Rad fluorescence.bio-rad.com; the information in the Web page is incorporated herein in its entirety).

I claim:

1. An isolated *Physalia* fluorescent protein (PFP) characterized by an emission wavelength of about 456 nm, when said PFP is excited at an excitation wavelength of 221 nm.

2. An isolated *Physalia* fluorescent protein (PFP) characterized by an emission wavelength of about 421 nm, when said PFP is excited at an excitation wavelength of 222 nm.

3. An isolated *Physalia* fluorescent protein (PFP) characterized by an emission wavelength of about 600 nm, when said PFP excited at an excitation wavelength of 222 nm.

4. An isolated *Physalia* fluorescent protein (PFP) characterized by an emission wavelength of about 597 nm, when said PFP is excited at an excitation wavelength of 301 nm.

5. An isolated *Physalia* fluorescent protein (PFP) characterized by an emission wavelength of about 598 nm, when said PFP is excited at an excitation wavelength of 301 nm.

6. An isolated *Physalia* fluorescent protein (PFP) characterized by an emission wavelength of about 600 nm, when said PFP is excited at an excitation wavelength of 301 nm.

7. An isolated *Physalia* fluorescent protein (PFP) characterized by an emission wavelength in a range of about 888–898 nm, when said PFP is excited at an excitation wavelength of 301 nm.

8. An isolated *Physalia* fluorescent protein (PFP) characterized by an emission wavelength of about 888 nm, when said PFP is excited at an excitation wavelength of 301 nm.

9. An isolated *Physalia* fluorescent protein (PFP) characterized by an emission wavelength of about 838 nm, when said PFP is excited at an excitation wavelength of 421 nm.

10. An isolated *Physalia* fluorescent protein (PFP) characterized by an emission wavelength of about 900 nm, when said PFP is excited at an excitation wavelength of 450 nm.

11. An isolated *Physalia* fluorescent protein (PFP) characterized by an emission wavelength of about 898 nm, when said PFP is excited at an excitation wavelength of 451 nm.

12. The *Physalia* fluorescent protein (PFP) of any one of claims 1–11, wherein said protein is further characterized by a molecular weight of about 10–15 kDa.

13. The *Physalia* fluorescent protein (PFP) of any one of claims 1–11, wherein said protein is further characterized by a molecular weight of about 35–40 kDa.

14. The *Physalia* fluorescent protein (PFP) of any one of claims 1–11, wherein said protein is of the species *P. utriculus*.

* * * * *